(12) United States Patent
Hsiao et al.

(10) Patent No.: US 8,722,900 B2
(45) Date of Patent: May 13, 2014

(54) PROCESS FOR CABAZITAXEL, AND INTERMEDIATES THEREOF

(71) Applicant: Scinopharm Taiwan, LTD., Shan-Hua (TW)

(72) Inventors: TsungYu Hsiao, Kaohsiung (TW); Julian Paul Henschke, Summertown (AU); HsinChang Tseng, Tainan (TW)

(73) Assignee: ScinoPharm Taiwan, Ltd., Shan-Hua (TW)

( * ) Notice: Subject to any disclaimer, the term of this patent is extended or adjusted under 35 U.S.C. 154(b) by 0 days.

(21) Appl. No.: 13/664,378

(22) Filed: Oct. 30, 2012

(65) Prior Publication Data

US 2013/0116444 A1  May 9, 2013

Related U.S. Application Data

(60) Provisional application No. 61/553,751, filed on Oct. 31, 2011.

(51) Int. Cl.
*C07D 409/14* (2006.01)
*C07D 413/14* (2006.01)
*C07D 305/14* (2006.01)

(52) U.S. Cl.
USPC .................. 548/215; 549/21; 549/33; 549/37

(58) Field of Classification Search
None
See application file for complete search history.

(56) References Cited

U.S. PATENT DOCUMENTS

| 5,847,170 A | 12/1998 | Bouchard et al. |
| 5,962,705 A | 10/1999 | Didier et al. |
| 6,593,482 B2 | 7/2003 | Bouchard et al. |
| 7,241,907 B2 | 7/2007 | Didier et al. |
| 2009/0221688 A1 | 9/2009 | Machado et al. |
| 2012/0149925 A1 | 6/2012 | Kung et al. |

FOREIGN PATENT DOCUMENTS

| EP | 2330100 A1 | 6/2011 |
| WO | 95/33737 A1 | 12/1995 |

OTHER PUBLICATIONS

Zhang et al., "A new synthesis route of cabazitaxel," Journal of Chinese Pharmaceutical Science, Online Sep. 15, 2012, vol. 5, pp. 472-476.
Kant et al., "A Chemoselective Approach to Functionalize the C-10 Position of 10-Deacetylbaccatin III Synthesis and Biological Properties of Novel C-10 Taxol® Analogues," Tetrahedron Letters, 1994, vol. 35, No. 31, pp. 5543-5546.
Ojima et al., "Syntheses and Structure—Activity Relationships of the Second-Generation Antitumor Taxoids: Exceptional Activity against Drug-Resistant Cancer Cells," 1996, J. Med. Chem., vol. 39, pp. 3889-3896.
J. Chem. Research (S), 1995, pp. 204-205.
Synthesis, 1990, pp. 89-103.
Tetrahedron, 1994, 50, pp. 3721-3742.
Tetrahedron, 1988, 29, pp. 2963-2966.
Bouchet et al., "Cabazitaxel, a new taxane with favorable properties," Drugs of Today, 2010, 46(10): 735-742.
PCT/IB2012/002846, International Search Report and Written Opinion, mailed Jun. 21, 2013, 8 pages.

*Primary Examiner* — Kamal Saeed
(74) *Attorney, Agent, or Firm* — Kilpatrick Townsend & Stockton LLP

(57) ABSTRACT

The present invention relates to processes for making cabazitaxel, cabazitaxel analogues and intermediates thereof. The invention provides novel compounds useful in the synthesis of cabazitaxel.

27 Claims, 13 Drawing Sheets

PROCESS FOR CABAZITAXEL, AND INTERMEDIATES THEREOF

CROSS-REFERENCES TO RELATED APPLICATIONS

This application claims the benefit of priority to U.S. Provisional Application Ser. No. 61/553,751, filed Oct. 31, 2011, the entire content of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates to processes of making cabazitaxel and intermediates thereof. Jevtana® is an injectable antineoplastic medicine whose active pharmaceutical ingredient (API), cabazitaxel, belongs to the taxane class and is closely related in both chemical structure and mode of action to the anticancer drugs paclitaxel (Taxol®) and docetaxel (Taxotere®). Cabazitaxel is prepared by semi-synthesis from 10-deacetylbaccatin III (10-DAB) which is extracted from yew tree needles. The chemical name of cabazitaxel is (2α,5β,7β,10β,13α)-4-acetoxy-13-({(2R,3S)-3-[(tert-butoxycarbonyl)amino]-2-hydroxy-3-phenylpropanoyl}oxy)-1-hydroxy-7,10-dimethoxy-9-oxo-5,20-epoxy-tax-11-en-2-yl benzoate and is marketed as a 1:1 acetone solvate (propan-2-one), having Formula A shown below. The acetone solvate of cabazitaxel is a white to off-white powder with a molecular formula of $C_{45}H_{57}NO_{14} \cdot C_3H_6O$ and a molecular weight of 894.01 grams/mole for the acetone solvate and 835.93 grams/mole for the solvent-free form.

Formula A

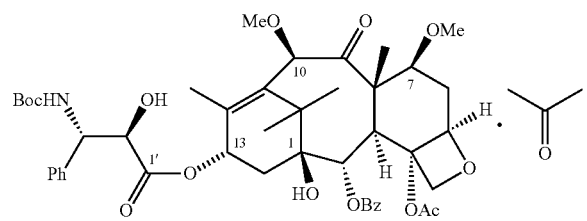

Cabazitaxel (also called dimethoxy docetaxel) is a dimethyl derivative of docetaxel, which itself is semi-synthetic, and was originally developed by Rhone-Poulenc Rorer and was approved by the U.S. Food and Drug Administration (FDA) for the treatment of hormone-refractory prostate cancer on Jun. 17, 2010. Cabazitaxel is a microtubule inhibitor. The acetone solvate crystalline form of cabazitaxel and a process for its preparation is disclosed in the U.S. Pat. No. 7,241,907.

U.S. Pat. No. 5,847,170 describes cabazitaxel and its preparation methods. One of the methods described in U.S. Pat. No. 5,847,170 includes a step-wise methylation of 10-DAB (the step-wise methylation method is shown in FIG. 1) to provide the key intermediate (2αR,4S,4αS,6R,9S,11S,12S,12αR,12βS)-12β-acetoxy-9,11-dihydroxy-4,6-dimethoxy-4α,8,13,13-tetramethyl-5-oxo-2α,3,4,4α,5,6,9,10,11,12,12α,12β-dodecahydro-1H-7,11-methanocyclodeca[3,4]benzo[1,2-b]oxet-12-yl benzoate, herein referred to as 7,10-di-O-methyl-10-DAB (XVa). The intermediate XVa is coupled with the 3-phenylisoserine side chain derivative VI to provide XVa', which is followed by removal of the oxazolidine protecting group from the side chain of XVa' to give cabazitaxel.

Another method described in U.S. Pat. No. 5,847,170 utilizes methylthiomethyl (MTM) ethers as shown in FIG. 2. MTM ethers can be prepared from alcohols using two common methods. One method comprises deprotonation of an alcohol with a strong base to form an alkoxide followed by alkylation of the alkoxide with a methylthiomethyl halide. This approach is only useful when the alcohol is stable to treatment with a strong base. 10-DAB and some of its derivatives in which C7-OH is not protected displays so instability in the presence of strong bases and epimerization of the C7-OH can occur upon contact of 10-DAB and some of its derivatives in which C7-OH is not protected with strong bases. Another method for the synthesis of MTM ethers from alcohols utilizes $Ac_2O$ and DMSO. One disadvantage of this method is that it can also lead to the oxidation of alcohols to aldehydes or ketones. For example when the synthesis of the 10-di-O-MTM derivative of 10-DAB without protecting groups at the C13 hydroxyl group is attempted undesired oxidation of the C13-OH to its corresponding ketone occurs.

U.S. Pat. No. 5,962,705 discloses a method for dialkylation of 10-DAB and its derivatives to furnish 7,10-di-O-alkyl derivatives, as shown in FIG. 3. This has been demonstrated as a one-step, one-pot reaction, however, provides the best isolated yield when potassium hydride is used at −30° C. From an industrial point of view, the use of low reaction temperature is less favorable than using ambient temperature. Furthermore the use of a strong base can cause some epimerization of the C7-OH chiral center with an associated loss of yield. Potassium hydride is a very reactive base and must be treated with great caution.

Accordingly, there is a need for an alternative processes for the preparation of cabazitaxel and its key intermediate, 7,10-di-O-methyl-10-DAB (XVa) that is short in number of synthetic steps and avoids the use of low temperatures and strong bases such as metal hydrides in the C7-O methyl ether formation step. Such a process would also be useful for the preparation of analogues of cabazitaxel wherein the C7-O and C10-O functional groups were substituted with other alkyl groups.

BRIEF SUMMARY OF THE INVENTION

The present invention relates to novel processes of making 7,10-di-O-methyl-10-DAB, a key cabazitaxel intermediate (Formula B below); cabazitaxel (Formula C, below); and analogues thereof.

Formula B

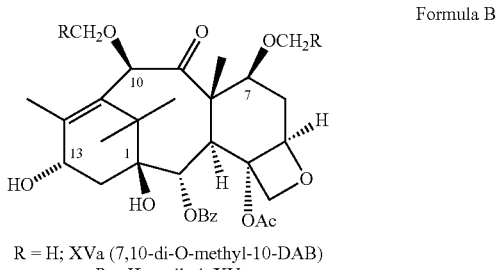

R = H; XVa (7,10-di-O-methyl-10-DAB)
R = H or alkyl; XV

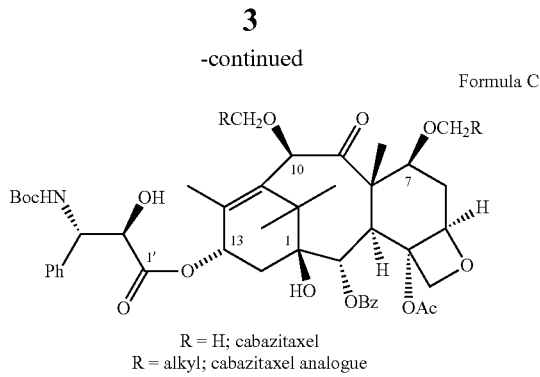

Formula C

R = H; cabazitaxel
R = alkyl; cabazitaxel analogue

In one aspect of the present invention, a process for the synthesis of cabazitaxel and its analogues includes the use of 10-DAB derivatives that possess 1,3-dithian-2-yl, or 1,3-dithiolan-2-yl, or 1,3-dithiolan-4-en-2-yl, or a 1,3-benzodithiolan-2-yl groups at both the C7-O and C10-O positions (FIG. 4). Derivatization of the C7-O and C10-O positions can be conducted before or after the C13-O position is functionalized, providing flexible routes to the desired compounds.

In another aspect of the present invention, a process for the synthesis of cabazitaxel and its analogues includes the use of 10-DAB derivatives that possess 1,3-dithian-2-yl, or 1,3-dithiolan-2-yl, or 1,3-dithiolan-4-en-2-yl, or a 1,3-benzodithiolan-2-yl groups at the C7-O position (FIG. 5)

In another aspect of the invention, novel compounds useful in the synthesis of cabazitaxel are provided.

DETAILED DESCRIPTION OF THE INVENTION

I. General

Figure 1:
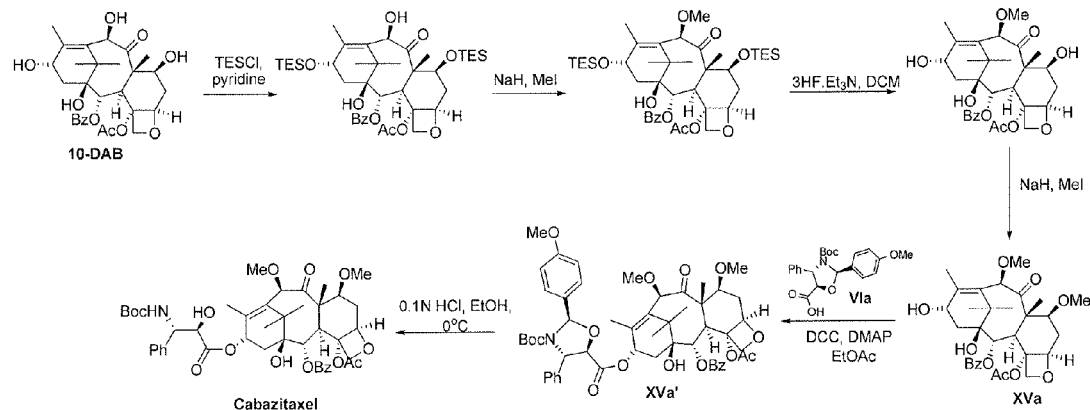
FIG. 1 shows the chemistry employed in the examples of U.S. Pat. No. 5,847,170.

The present invention provides novel a method employing latent/masked-methyl groups for the synthesis of cabazitaxel and XVa, a key cabazitaxel intermediate. The method also provides cabazitaxel analogs and novel compounds useful for the synthesis of cabazitaxel. Surprisingly, the process affords cabazitaxel intermediates using milder conditions than previously known in the art. Accordingly, the present invention provides an improved route to a compound that addresses important medical needs. Furthermore, the route may provide access to other compounds with beneficial therapeutic properties.

II. Definitions

As used herein, the term "taxane" refers to compound having a structural skeleton similar to diterpene natural products, also called taxanes, initially isolated from yew trees (genus *Taxus*). Taxanes are generally characterized by a fused 6/8/6 tricyclic carbon backbone, and the group includes natural products and synthetic derivatives. Examples of taxanes include, but are not limited to, paclitaxel, docetaxel, and cabazitaxel.

As used herein, the term "dithiane" refers to a six-membered heterocyclic functional group containing two sulfur atoms. The dithianes useful in the present invention may be saturated or unsaturated. Dithiane derivatives include dithian-2-ylium salts. Dithianes may be substituted with alkyl groups or aryl groups, as well as with leaving groups for reaction with suitable nucleophiles.

As used herein, the term "dithiolane" refers to a five-membered heterocyclic functional group containing two sulfur atoms. The dithiolanes useful in the present invention may be saturated or unsaturated. Dithiolane derivatives include dithiolan-2-ylium salts and dithiolium salts. Dithiolanes may be substituted with alkyl groups or aryl groups, as well as with leaving groups for reaction with suitable nucleophiles.

The term "alkyl," by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 10 carbon atoms. For example, an alkyl group can contain 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term "alkenyl" refers to either a straight chain or branched hydrocarbon having at least one double bond. Unless otherwise specified, the alkenyl groups of the present invention contain 2 to 6 carbon atoms. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkynyl" refers to either a straight chain or branched hydrocarbon having at least one triple bond. Unless otherwise specified, the alkynyl groups of the present invention contain 2 to 6 carbon atoms. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the terms "halide," "halo," or "halogen," by themselves or as part of another substituent, mean a fluorine, chlorine, bromine, or iodine atom.

As used herein, the terms "aryl" and "aromatic ring," by themselves or as part of another substituent, refer to a polyunsaturated, hydrocarbon group which can be a single ring or multiple rings (up to three rings) which are fused together or linked covalently. Non-limiting examples of aryl groups include phenyl, naphthyl and biphenyl.

As used herein, the term "arylalkyl" refers to a radical having an alkyl component and an aryl component, where the alkyl component links the aryl component to the point of attachment. The alkyl component is as defined above, except that the alkyl component is at least divalent in order to link to the aryl component to the point of attachment. In some instances, the alkyl component can be absent. The aryl component is as defined above. Examples of arylalkyl groups include, but are not limited to, benzyl and phenylethyl.

As used herein, the term "alkoxy," by itself or as part of another substituent, refers to an alkyl group having an oxygen atom that connects the alkyl group to the point of attachment.

Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

As used herein, the term "hydroxyalkyl" refers to alkyl as defined above where at least one of the hydrogen atoms is substituted with a hydroxy group. For example, hydroxyalkyl includes hydroxy-methyl, hydroxy-ethyl (1- or 2-), hydroxy-propyl (1-, 2- or 3-), hydroxy-butyl (1-, 2-, 3- or 4-), hydroxy-pentyl (1-, 2-, 3-, 4- or 5-), hydroxy-hexyl (1-, 2-, 3-, 4-, 5- or 6-), 1,2-dihydroxyethyl, and the like.

As used herein, the term "thio" refers to a sulfur-containing radical wherein a sulfur atom is the point of attachment. The sulfur atom can be substituted with additional groups including, but not limited to, alkyl groups and aryl groups as defined above. The term "mercapto" refers to a radical having the structure —S—H.

As used herein, the term "acyl," by itself or as part of another substituent, refers to a radical containing an alkyl group, defined as above, bound to the carbon atom of a carbonyl group, the carbonyl carbon atom further being the point of attachment of the radical.

As used herein, the term "formyl," by itself or as part of another substituent, refers to a radical containing a hydrogen atom bound to the carbon atom of a carbonyl group, the carbonyl carbon atom further being the point of attachment of the radical.

As used herein, the term "aroyl," by itself or as part of another substituent, refers to a radical containing an aryl group, defined as above, bound to the carbon atom of a carbonyl group, the carbonyl carbon atom further being the point of attachment of the radical. Examples of aryol groups include, but are not limited to, furoyl (containing a furan group bound to a carbonyl group) and thenoyl (containing a thiophene group bound to a carbonyl group).

As used herein, the term "carbamoyl" refers to a radical containing an amino group bound to the carbon atom of a carbonyl group, the carbonyl carbon further being the point of attachment of the radical. The amino group may be functionalized with additional substituents. For example, an alkylcarbamoyl group contains an alkyl group bound to the amino group, while a dialkylcarbamoyl group contains two alkyl groups bound to the amino group.

As used herein, the term "hydrodesulfurization" refers to the removal of a sulfur-containing functional group, such as a dithiane or dithiolane, to provide a saturated carbon center at the site where the sulfur-containing functional group was located. The hydrodesulfurization can be carried out using conditions known in the art or any other suitable means.

As used herein, the term "strong base" generally refers to a base whose conjugate acid possesses a $pK_a$ around or above 15. Examples of strong bases include, but are not limited to, alkali metal hydrides, alkali metal alkoxides, alkali metal amides, alkyllithiums, and silver oxide.

As used herein, the term "weak base" generally refers to a base whose conjugate acid possesses a $pK_a$ around or below 12. Examples of weak bases include, but are not limited to, pyridine, pyridine derivatives, tertiary amines, 1,8-diazabicyclo[5.4.0]undec-7-ene, 1,5-diazabicyclo[4.3.0]non-5-ene, saturated heterocyclic bases, and aromatic heterocyclic bases.

As used herein, the term "protecting group" refers to a compound that renders a functional group unreactive, but is also removable so as to restore the functional group to its original state. Such protecting groups are well known to one of ordinary skill in the art and include compounds that are disclosed in *Protective Groups in Organic Synthesis*, 4th edition, T. W. Greene and P. G. M. Wuts, John Wiley & Sons, New York, 2006, which is incorporated herein by reference in its entirety.

As used herein, the term "desilylation agent" refers to any substance suitable for remove a silyl protecting group from a functional group. Examples of desilylation agents include, but are not limited to, tetrabutylammonium fluoride (TBAF), hydrofluoric acid, cesium fluoride, potassium fluoride, hydrochloric acid, toluenesulfonic acid, and trifluoroacetic acid.

As used herein, the term "esterifying" refers to the conversion of an alcohol or a carboxylic acid to an ester. Esterification may include conversion of the carboxylic acid or alcohol to an intermediate compound suitable for conversion to the ester product. The intermediate compounds may be isolated prior to the final esterification step or converted to the ester product in situ without isolation.

Certain specific compounds of the present invention contain both basic and acidic functionalities that allow the compounds to be converted into either base or acid addition salts. "Pharmaceutically acceptable salts" include salts of the active compounds which are prepared with relatively nontoxic acids or bases, depending on the particular substituents found on the compounds described herein. See, for example, Berge, S. M., et al, "Pharmaceutical Salts", *Journal of Pharmaceutical Science*, 1977, 66, 1-19.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

III. Embodiments of the Invention

The present invention provides a method that is useful for the preparation of a key intermediate XVa and its 7,10-di-O-alkyl analogues XV, which are very useful for the manufacture of cabazitaxel and analogues of cabazitaxel. The invention also provides methods that is useful for preparation of key intermediate XVa' and its 7,10-di-O-alkyl analogues XV' that are useful for the manufacture of cabazitaxel and its analogues.

Figure 4:
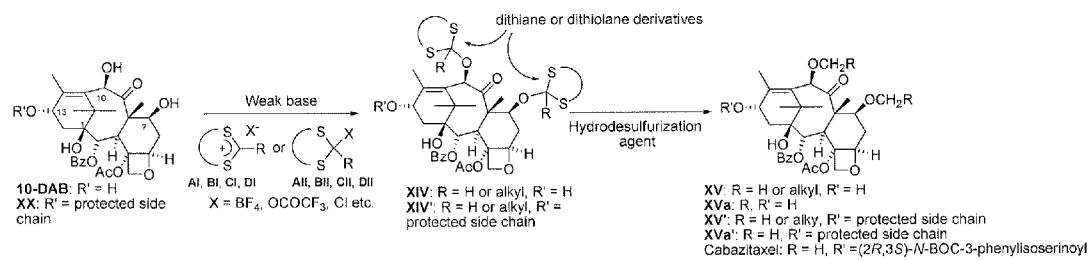
FIG. 4 shows key steps of the general synthetic scheme as per Method A/A' of the present invention for the synthesis of cabazitaxel and cabazitaxel analogues.

In some embodiments, 10-DAB derivatives XIV or XIV' that possess 1,3-dithian-2-yl, 1,3-dithiolan-2-yl, 1,3-dithiolan-4-en-2-yl, or 1,3-benzodithiolan-2-yl groups at both of C7-O and C10-O are used for the synthesis of cabazitaxel or analogues (FIG. 4).

Figure 5:
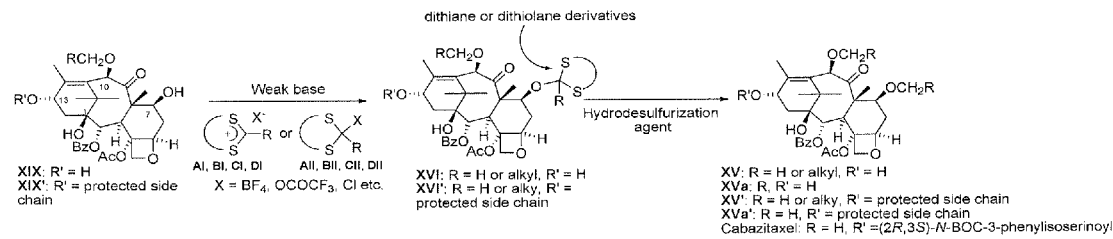
FIG. 5 shows key steps of the general synthetic scheme as per Method B/B' of the present invention for the synthesis of cabazitaxel and cabazitaxel analogues.

In other embodiments, 10-DAB derivatives XVI or XVI' that possess a 1,3-dithian-2-yl, 1,3-dithiolan-2-yl, 1,3-dithiolan-4-en-2-yl, or 1,3-benzodithiolan-2-yl group at C7-O are used for the synthesis of cabazitaxel or analogues (FIG. 5).

A 1,3-dithiane is a 6-membered ring moiety that contains two sulfur atoms displaced by one single carbon atom. A 1,3-dithiolane is a 5-membered ring moiety that contains two sulfur atoms displaced by one single carbon atom. These structural moieties may possess unsaturated carbon-carbon double bonds such as found in 1,3-benzodithiolanes, for example. Dithianes and dithiolanes useful in the present invention are summarized below. These sulfur-containing moieties function as latent alkyl groups, including methyl groups. That is, upon hydrodesulfurization they are converted into alkyl groups, including methyl groups. The hydrodesulfurization can be conducted using Raney Nickel (Raney-Ni or Ra-Ni) or related nickel-based catalysts (including nickel boride ("Ni$_2$B") and Ni$^o$-complexes called NiCRA (*Tetrahedron Lett.*, 1988, 29, 2963). 10-DAB derivatives that possess 1,3-dithian-2-yl (A), or 1,3-dithiolan-2-yl (B), or 1,3-dithiolan-4-en-2-yl (C), or a 1,3-benzodithiolan-2-yl (D) groups at either or both of C7-O and C10-O are prepared by contacting 10-DAB or its derivatives in the presence of a weak base with 1,3-dithiane derivatives and 1,3-dithiolane derivatives such as 1,3-dithian-2-ylium salts (AI), 1,3-dithiolan-2-ylium salts (BI), 1,3-dithiolium salts (CI), or 1,3-benzodithiolium salts (DI), or alternatively with 1,3-dithiane derivatives (AII) or 1,3-dithiolane derivatives (BII)/(CII)/(DII) that possess a leaving group, X, at the C2 position. In some embodiments of the present invention the 1,3-dithian-2-ylium salts (AI), 1,3-dithiolan-2-ylium salts (BI), and 1,3-benzodithiolium salts (DI) are 1,3-dithian-2-ylium trifluoroacetate (AIa), 1,3-dithiolan-2-ylium trifluoroacetate (BIa) and 1,3-benzodithiolium tetrafluoroborate (DIa). The 1,3-dithian-2-ylium salts (AI) and 1,3-dithiolan-2-ylium salts (BI) salts can be prepared by mono oxidation of 1,3-dithianes and 1,3-dithiolanes followed by treatment with a salt forming agent such as trifluoroacetic anhydride as report in the arts (for example, see *Tetrahedron*, 1994, 50, 3721-3742 and *J. Chem. Research (S)*, 1995, 204-205). 1,3-benzodithiolium tetrafluoroborate is a commercially available compound. Weak bases include pyridine, pyridine derivatives, imidazole, imidazole derivatives, and amines including tertiary amines such as Et$_3$N and diisopropylethylamine. Counter anions of the 1,3-dithian-2-ylium, 1,3-dithiolan-2-ylium, 1,3-benzodithiolium, and 1,3-dithiolium cations include, but are not limited to BF$_4$, OCOCF$_3$, and Cl. The C2 position of the 1,3-dithiane and 1,3-dithiolane moieties can be substituted with either H or an unbranched or branched C$_1$-C$_5$ alkyl chain, R. Suitable leaving groups X include, but are not limited to, halides, tosylates, mesylates, triflates, nosylates, and the like.

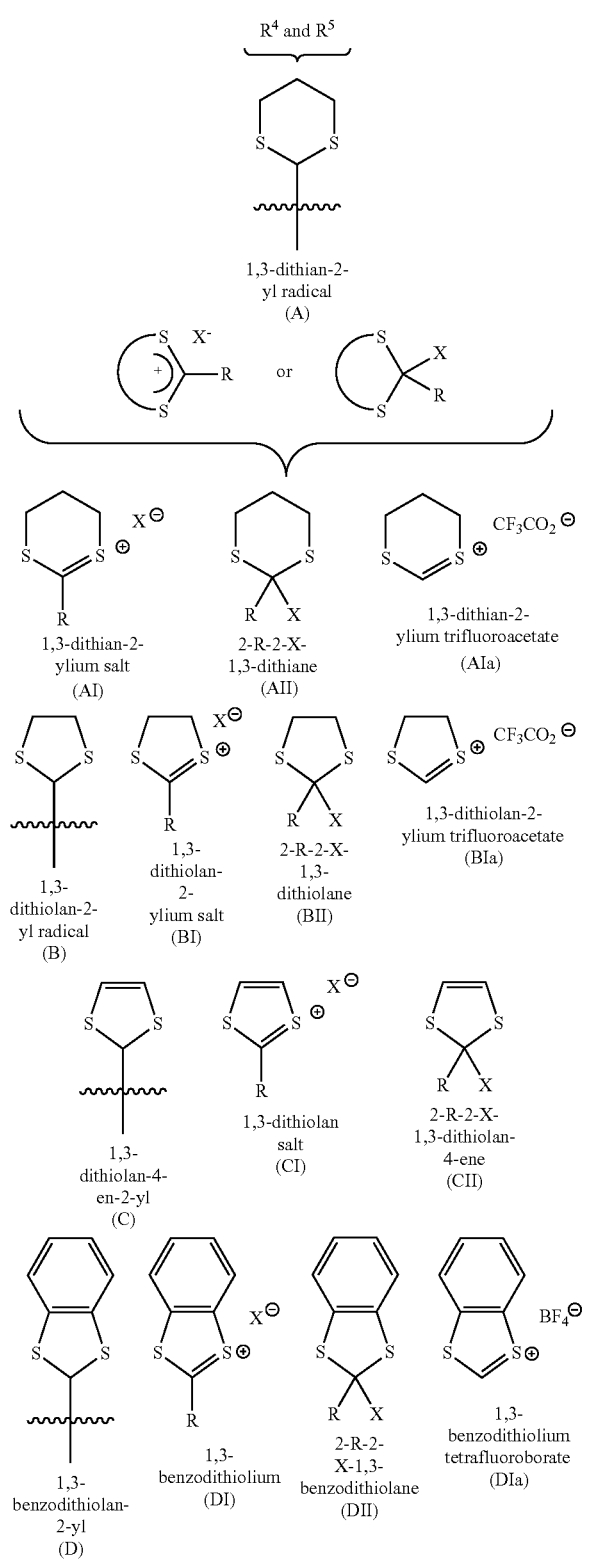

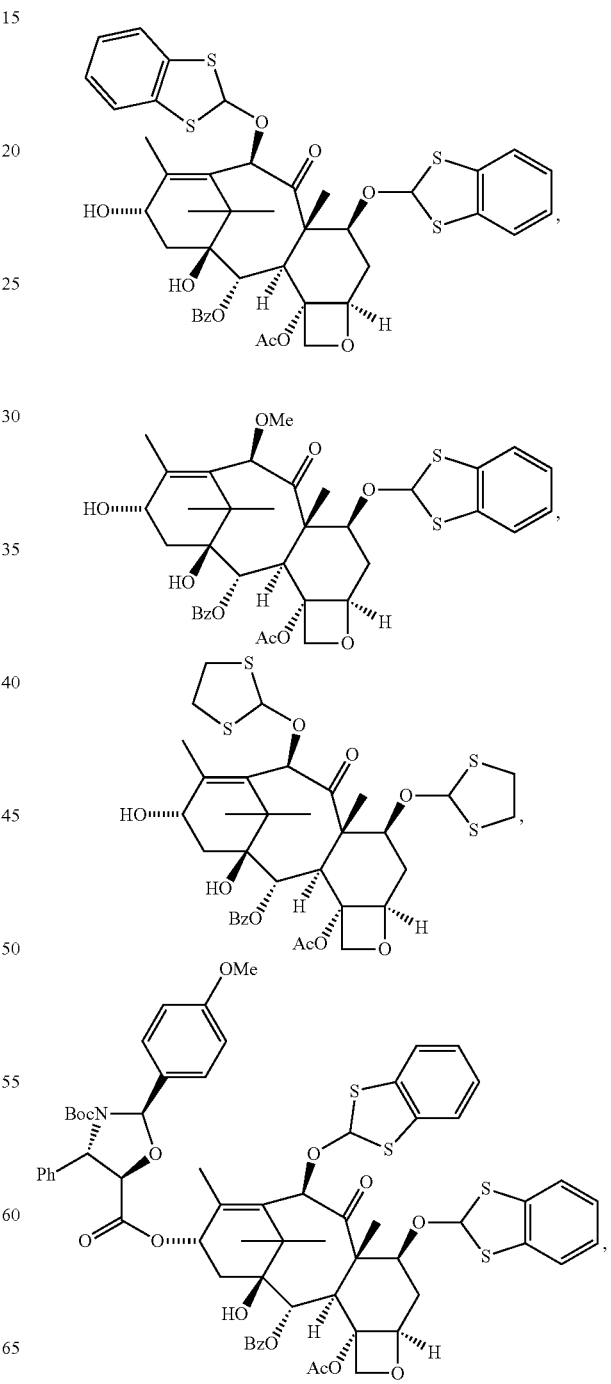

2963-2966). Alternative hydrodesulfurization agents include trialkyltin hydrides (such as $Bu_3SnH$), trialkylgermanium hydrides (such as $Bu_3GeH$) (with radical initiators such as 2,2'-azobis(2-methylpropionitrile) (AIBN), triethylborane or others), and $[NiCl_2]6H_2O$ in the presence of hydrogen, $NaBH_4$, or other reducing agents.

Figure 6:
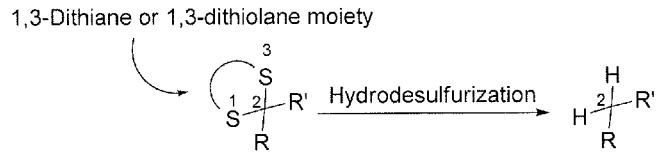
FIG. 6 shows the general scheme for the hydrodesulfurization reaction.

In some embodiments, a process is provided for preparing 7,10-di-O-alkyl taxane derivatives, wherein 1,3-dithiolan-2-yl derivatives or 1,3-dithian-2-yl derivatives are used as synthetic intermediates. In some embodiments, the 1,3-dithiolane derivatives or 1,3-dithiane derivatives are selected from:

1,3-dithiolanes and 1,3-dithianes can be hydrodesulfurized to provide alkanes (FIG. 6). The hydrodesulfurization can be conducted using heterogeneous Raney Nickel, with or without an atmosphere of hydrogen, but other forms of nickel and other transition metals can be used instead (for example, see *Synthesis*, 1990, 89-103; *Tetrahedron Letters*, 1988, 29, -continued

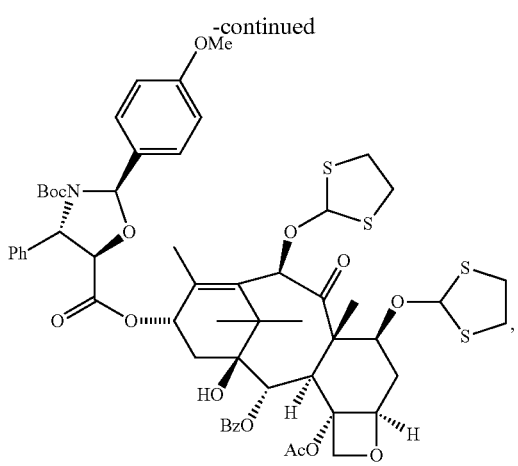

, and

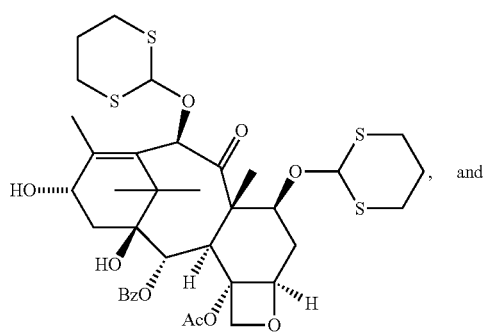

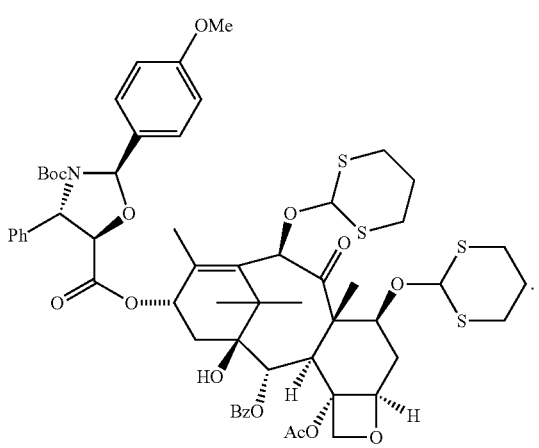

Accordingly, the present invention provides a process for preparing a compound of formula (I):

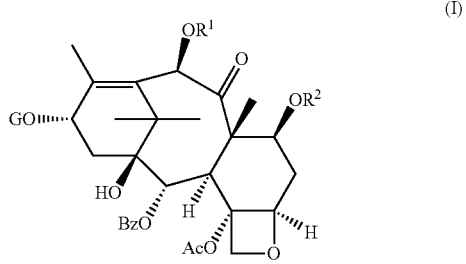
(I)

The process includes:

a) contacting 10-deacetylbaccatin III (10-DAB) of formula (II)

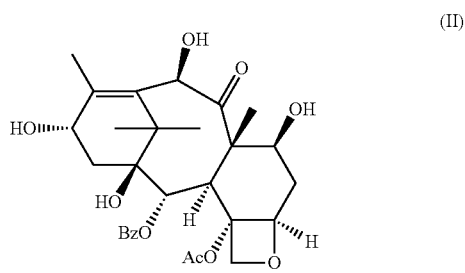
(II)

with 1,3-dithiolane derivatives or 1,3-dithiane derivatives, to obtain a compound of formula (V)

(V)

GO and b) converting said compound of formula (V) to a compound of formula (I); wherein
  each of $R^1$ and $R^2$, which may be identical or different, is an unbranched or a branched $C_1$-$C_6$ alkyl chain;
  each of $R^4$ and $R^5$, which may be identical or different, is a 1,3-dithian-2-yl radical, a 1,3-dithiolan-2-yl radical, a 1,3-dithiolan-4-en-2-yl radical, or a 1,3-benzodithiolan-2-yl radical; and
  G is H.

In some embodiments, 10-deacetylbaccatin III is treated with 1,3-dithiolane derivatives or 1,3-dithiane derivatives as described above in the presence of a weak base. In some embodiments, the weak base is pyridine, a tertiary amine, 1,8-diazabicyclo[5.4.0]undec-7-ene, 1,5-diazabicyclo[4.3.0]non-5-ene, a saturated heterocyclic base, a pyridine derivative or an aromatic heterocyclic base.

In yet another aspect, the present invention provides a process for preparing a compound of formula (I)

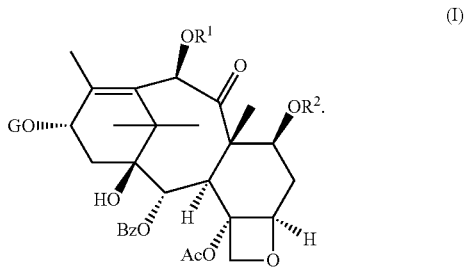
(I)

The process includes:

a) contacting 10-deacetylbaccatin III of formula (II)

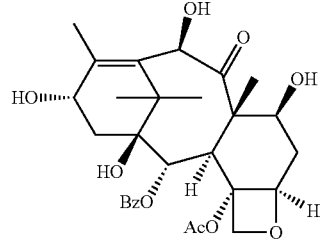

(II)

with a compound of (R")₃SiY (IVX) to obtain a compound of formula (VIII)

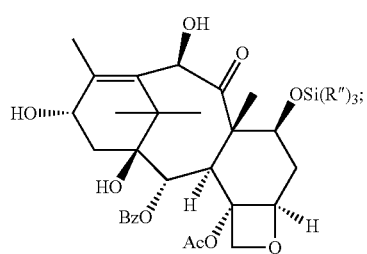

(VIII)

b) contacting the compound of formula (VIII) with an alkyl halide, a dialkyl sulfate, a trialkyl oxonium salt or an alkyl sulfonate in the presence of a strong base to obtain a compound of formula (IX)

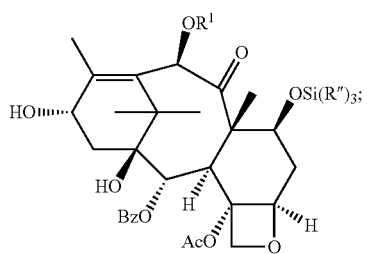

(IX)

c) contacting the compound of formula (IX) with a desilylation agent to obtain a compound of formula (X)

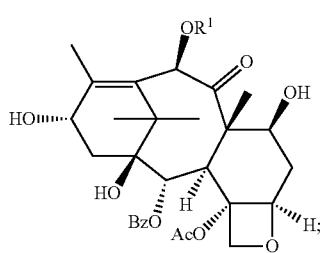

(X)

d) contacting the compound of formula (X) with dithiane derivatives or dithiolane derivatives, to obtain a compound of formula (VII)

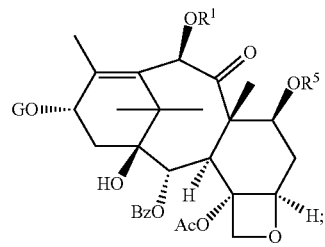

(VII)

and e) converting the compound of formula (VII) to the compound of formula (I); wherein each of $R^1$ and $R^2$, which may be identical or different, is an unbranched or a branched $C_1$-$C_6$ alkyl chain;

$R^5$ is a 1,3-dithian-2-yl radical, a 1,3-dithiolan-2-yl radical, a 1,3-dithiolan-4-en-2-yl radical, or a 1,3-benzodithiolan-2-yl radical;

R" is independently unbranched or branched $C_1$-$C_6$ alkyl or $C_6$-$C_{10}$ aryl;

G is H; and

Y is a halide.

In some embodiments, the transformation of an intermediate to the compound of formula (I) is conducted with a hydrodesulfurization agent which is selected from (i) Raney Nickel, (ii) [NiCl₂]6H₂O in the presence of NaBH₄, and (iii) transition metals. In some embodiments, the hydrodesulfurization reaction is conducted in the presence of a reducing agent or in the presence of a hydrogen source. In some embodiments, the hydrodesulfurization agent is Raney Nickel and the hydrodesulfurization reaction is conducted in the presence of a hydrogen source.

In still another aspect, the present invention provides a process for preparing a compound of formula (XIII)

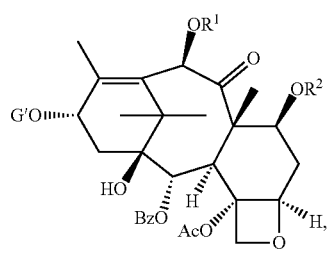

(XIII)

wherein G' is a side chain of formula (IV')

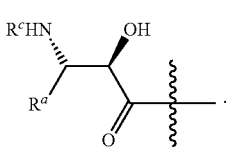

(IV')

The process includes converting a compound of formula (VA)

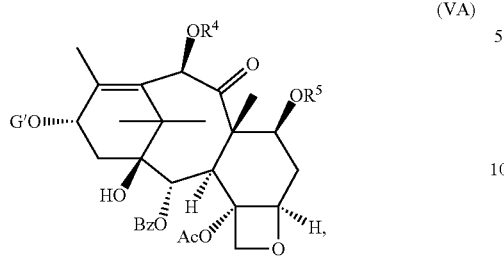

(VA)

wherein G' is a side chain of formula (IV)

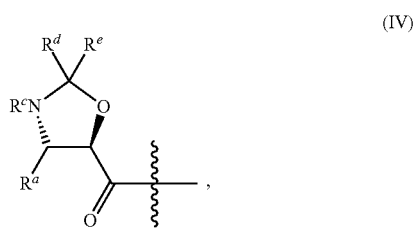

(IV)

to the compound of formula (XIII); wherein
each of $R^1$ and $R^2$, which may be identical or different, is unbranched or branched $C_1$-$C_6$ alkyl; and
each of $R^4$ and $R^5$, which may be identical or different, is a 1,3-dithian-2-yl radical, a 1,3-dithiolan-2-yl radical, a 1,3-dithiolan-4-en-2-yl radical, or a 1,3-benzodithiol-2-yl radical;
$R^a$ is branched or unbranched $C_1$-$C_8$ alkyl; branched or unbranched $C_2$-$C_8$ alkenyl; branched or unbranched $C_2$-$C_8$ alkynyl; or phenyl or naphthyl optionally substituted with one or more substituents selected from the group consisting of halo, alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonyl, carbamoyl, alkylcarbamoyl, dialkylcarbamoyl, cyano, nitro, and trifluoromethyl;
$R^c$ is benzoyl optionally substituted with one or more substituents independently selected from the group consisting of halo, $C_1$-$C_4$ alkyl, $C_1$-$C_4$ alkoxy, and trifluoromethyl; thenoyl; furoyl; or
$R^c$ is $R^3$—O—CO— wherein
$R^3$ is $C_1$-$C_8$ alkyl, $C_2$-$C_8$ alkenyl, $C_3$-$C_8$ alkynyl, $C_3$-$C_6$ cycloalkyl, or $C_4$-$C_6$ cycloalkenyl; each of which is optionally substituted with one or more substituents selected from the group consisting of cyano; carboxyl; $C_1$-$C_4$ alkoxycarbonyl; and phenyl optionally with one or more of halo, $C_1$-$C_4$ alkyl, and $C_1$-$C_4$ alkoxy; or
$R^3$ is phenyl or naphthyl, each of which is optionally substituted with one or more substituents selected from halo and $C_1$-$C_4$ alkyl; or
$R^3$ is 5-membered heteroaryl; and
$R^d$ and $R^e$ are independently selected from hydrogen, alkyl, aryl, halo, alkoxy, arylalkyl, haloalkyl and haloaryl; or taken together $R^d$ and $R^e$ form a 4- to 7-membered ring.
In some embodiments, conversion of an intermediate (VA) to a compound of formula (XIII) includes hydrodesulfurization and deprotection of the side chain protecting group in one reaction step or in separate reactions steps.

In some embodiments, the compound of formula (VA) is prepared by contacting a compound of formula (III)

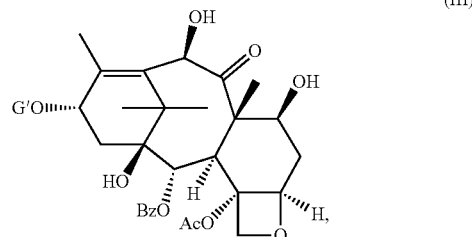

(III)

wherein G' is a side chain of formula (IV)

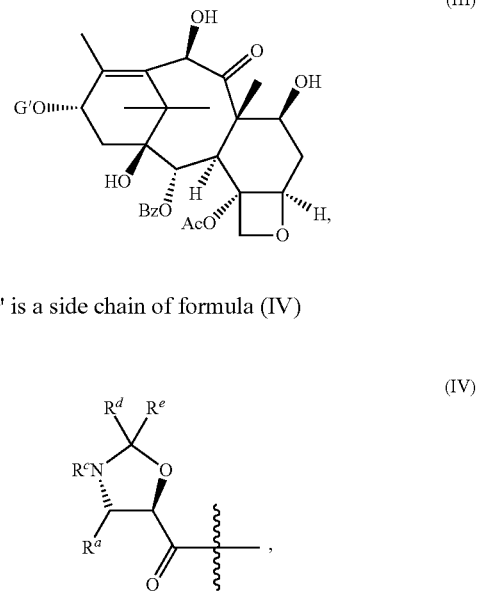

(IV)

with 1,3-dithiolane derivatives or 1,3-dithiane derivatives, to obtain the compound of formula (VA).

In some embodiments, the compound of formula (VA) is prepared by esterifying a compound of formula (V)

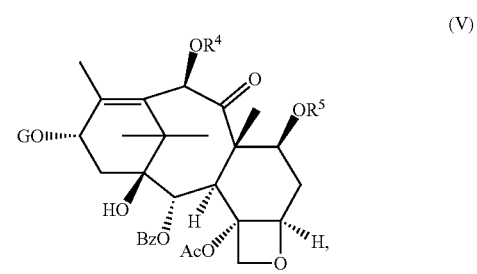

(V)

wherein G is H, with a compound of formula (VI)

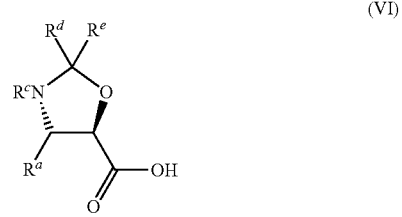

(VI)

to obtain the compound of formula (VA); wherein
each of $R^4$ and $R^5$, which may be identical or different, is a 1,3-dithian-2-yl radical, a 1,3-dithiolan-2-yl radical, a 1,3-dithiolan-4-en-2-yl radical or a 1,3-benzodithiol-2-yl radical; and
$R^a$, $R^c$, $R^d$, and $R^e$ are defined as above.

In yet another aspect, the present invention provides a process for preparing a compound of formula (XIII)

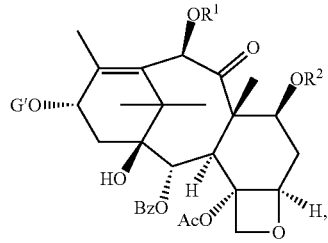 (XIII)

wherein G' is a side chain of formula (IV')

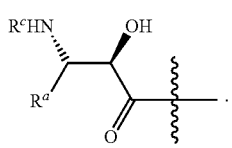 (IV')

The process includes:
a) esterifying a compound of formula (IX)

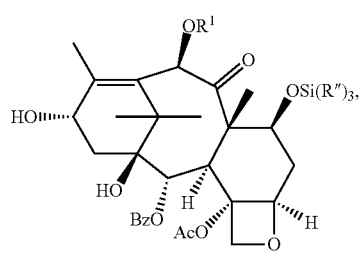 (IX)

with a compound of formula (VI)

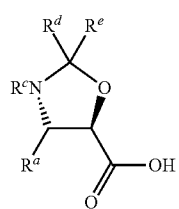 (VI)

to obtain a compound of formula (IXA)

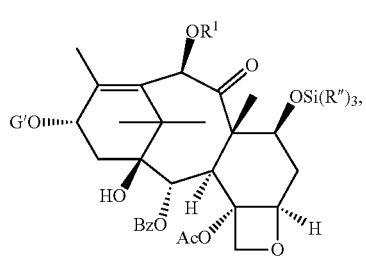 (IXA)

wherein G is a side chain of formula (IV)

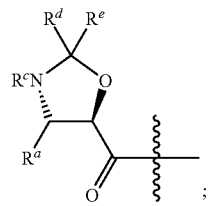 (IV)

b) converting the compound of formula (IXA) to a compound of formula (XA)

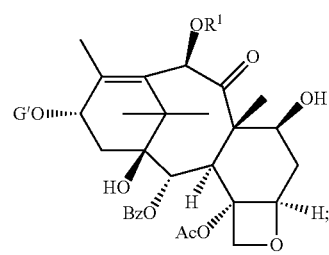 (XA)

c) converting the compound of formula (XA) by treatment with 1,3-dithiolane derivatives or 1,3-dithiane derivatives, to a compound of (XIIA)

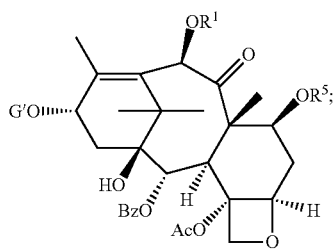 (XIIA)

and
d) converting the compound of formula (XIIA) to obtain the compound of formula (XIII); wherein
each of $R^1$ and $R^2$, which may be identical or different, is an unbranched or a branched $C_1$-$C_6$ alkyl chain;
$R^5$ is a 1,3-dithian-2-yl radical, a 1,3-dithiolan-2-yl radical, a 1,3-dithiolan-4-en-2-yl radical, or a 1,3-benzodithiol-2-yl radical;
R" is an unbranched or a branched $C_1$-$C_6$ alkyl chain or a $C_6$-$C_{10}$ aromatic ring; and
$R^a$, $R^c$, $R^d$, and $R^e$ are defined as above.

In some embodiments, conversion of an intermediate (XIIA) to a compound of formula (XIII) comprises hydrodesulfurization and deprotection of the side chain protecting group in one reaction step or in separate reactions steps.

In some embodiments of any of the processes described above, the strong base employed for C10-O alkylation, if used, is an alkali metal hydride, an alkali metal alkoxide, silver oxide, a mixture of an alkali metal amide and an alkali metal tert-butoxide, or a mixture of an alkyllithium and an alkali metal tert-butoxide.

In some embodiments of any of the processes described above, each of $R^1$ and $R^2$, which may be identical or different, is an unbranched or a branched $C_1$-$C_6$ alkyl chain. In some embodiments of any of the processes described above, each of $R^1$ and $R^2$ is a methyl group. In some embodiments of any of the processes described above, compounds of formula (I), if synthesized, can be further converted into cabazitaxel, with the proviso that each of $R^1$ and $R^2$ is a methyl group. In some embodiments of any of the processes described above, $R^a$, if present, is Ph; $R^c$, if present, is BOC; $R^d$, if present, is H; and $R^e$, if present, is 4-methoxyphenyl.

Some embodiments provide one or more following compounds:

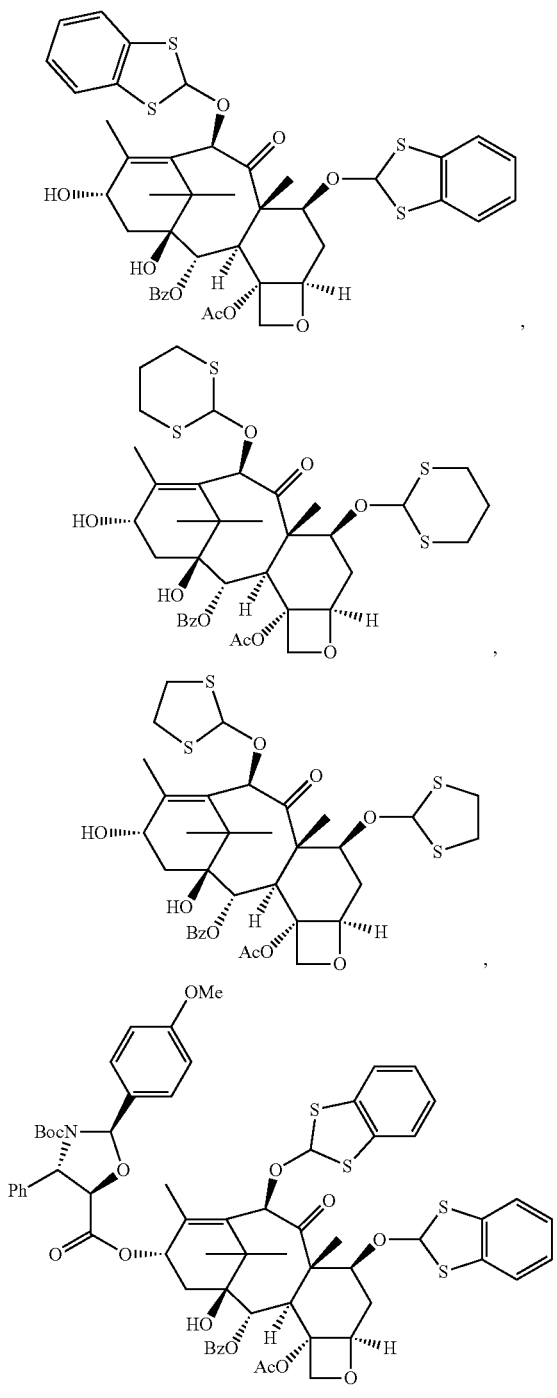

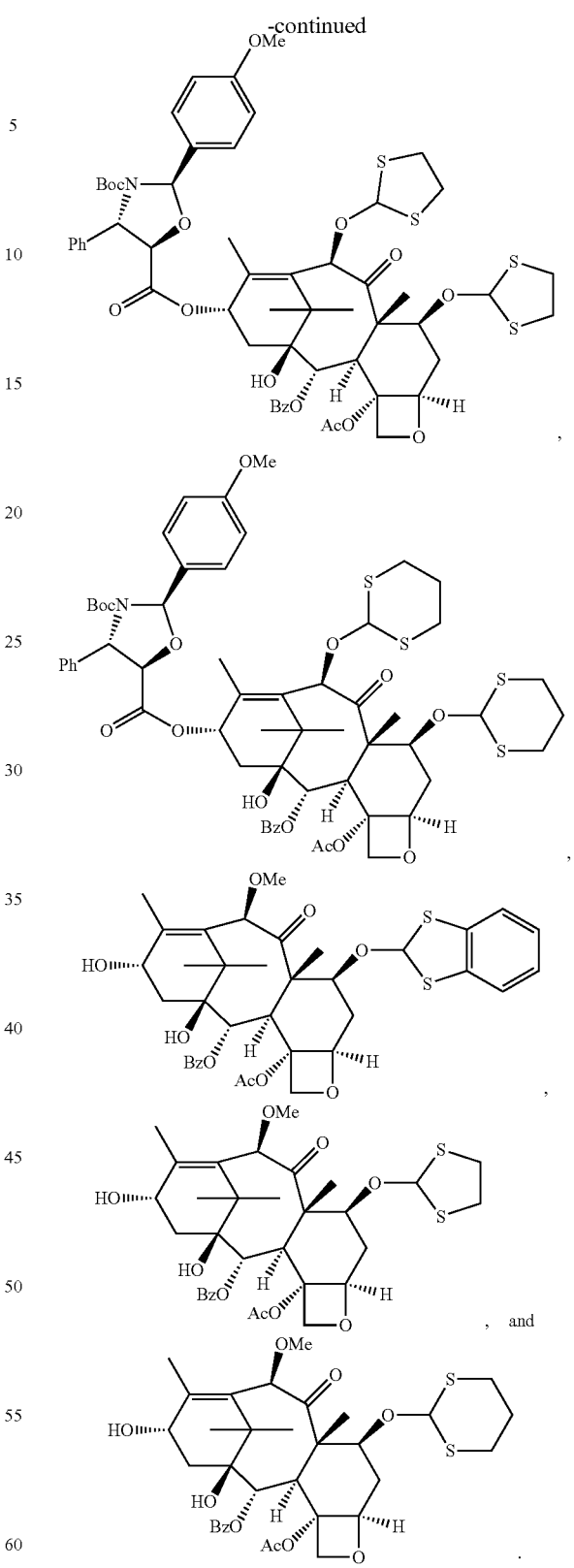

Figure 9:
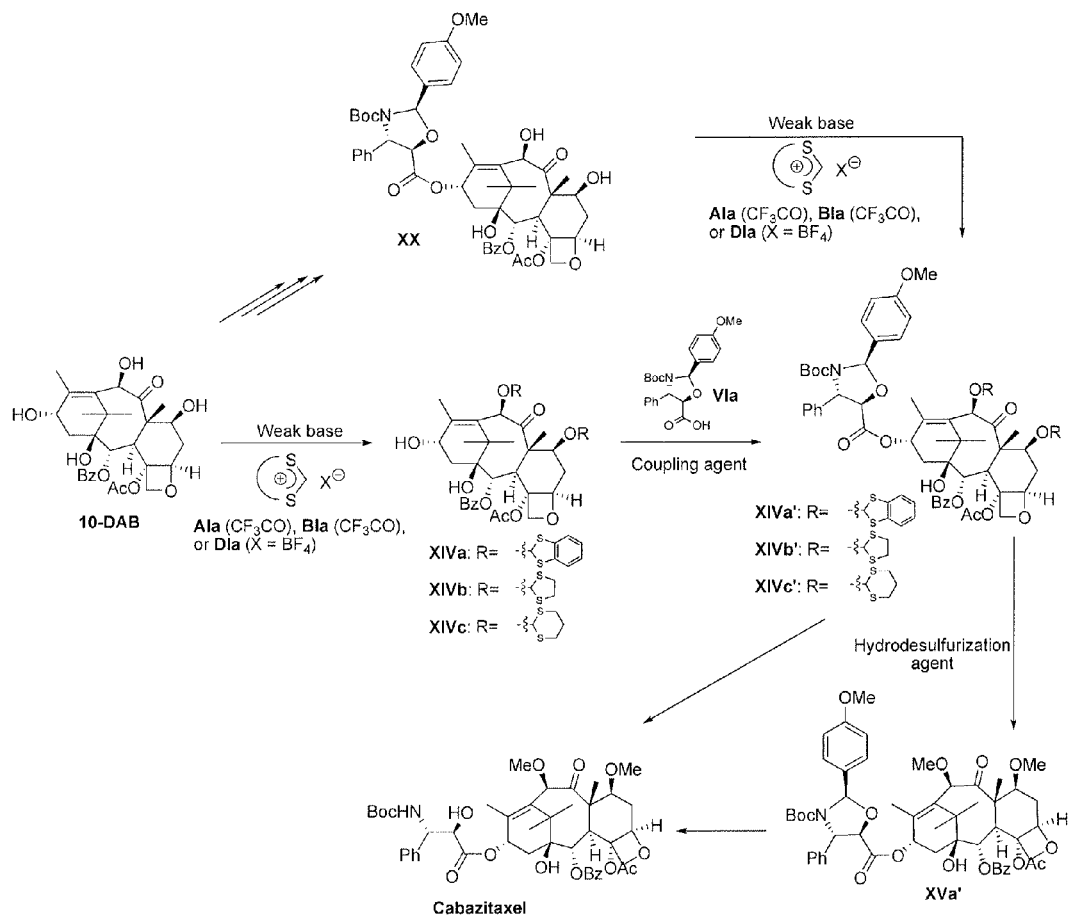
FIG. 9 shows the complete synthetic route of Method A' that can be used for conversion of 10-DAB, via XIV', to cabazitaxel.
Figure 10:
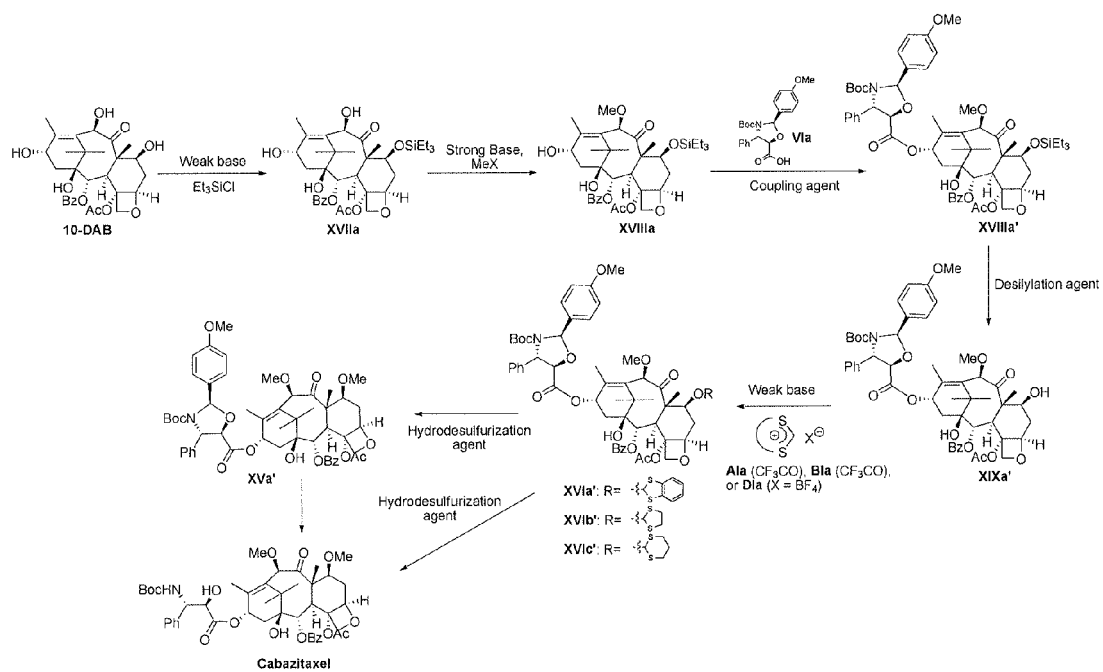
FIG. 10 shows the complete synthetic route of Method B' that can be used for conversion of 10-DAB, via XVI', to cabazitaxel.

The synthetic routes to cabazitaxel fall into two groups. One group includes Method A (FIG. 7) and Method B (FIG. 8), in which the hydrodesulfurization step is conducted in the absence of a C13-O protected 3-phenylisoserinoyl side chain (i.e., (2R,3S)-N-t-butoxycarbonyl-3-phenylisoserinoyl radical). The other group includes Method A' (FIG. 9) and Method B' (FIG. 10), in which the hydrodesulfurization step is conducted in the presence of a C13-O protected 3-phenylisoserinoyl side chain.

Figure 7:
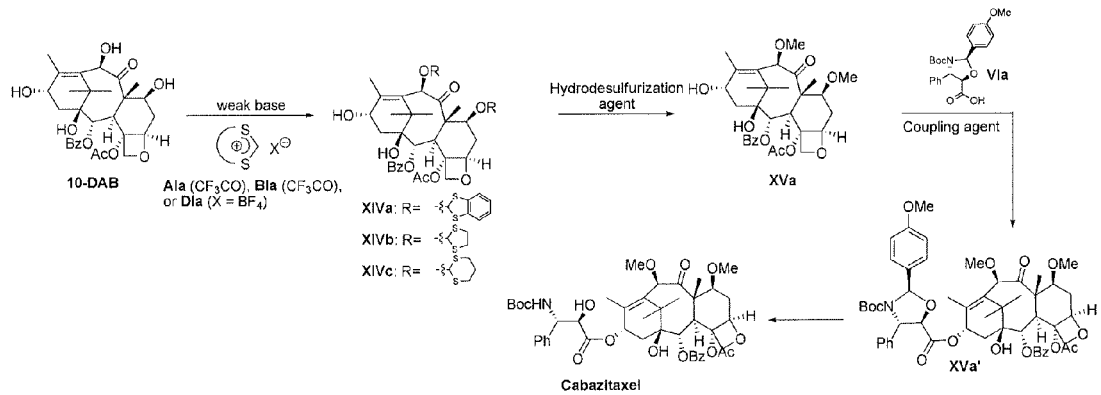
FIG. 7 shows the complete synthetic route of Method A that can be used for conversion of 10-DAB to cabazitaxel.
Figure 8:
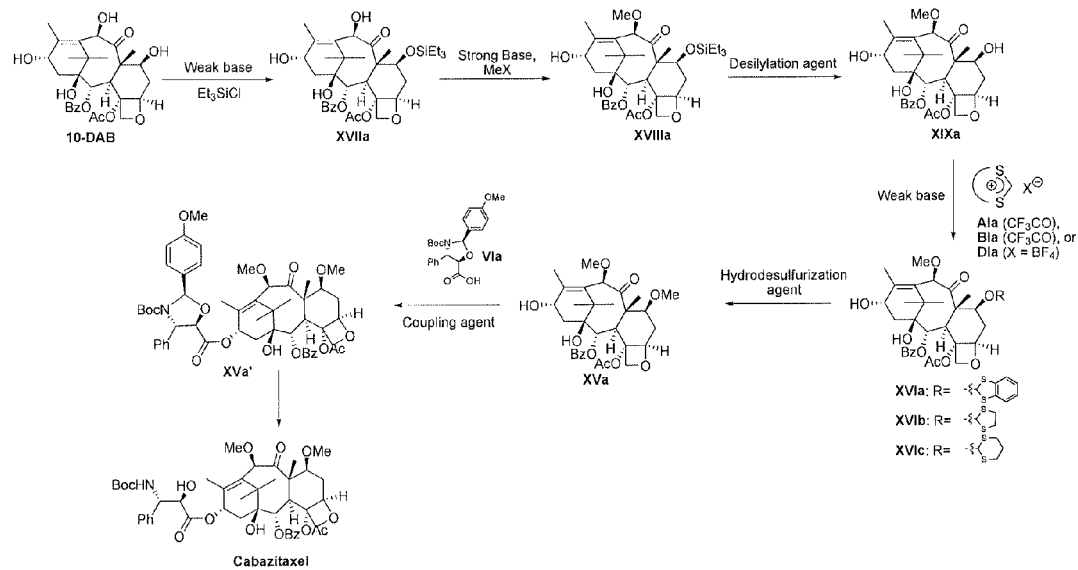
FIG. 8 shows the complete synthetic route of Method B that can be used for conversion of 10-DAB to cabazitaxel.

Method A and Method B utilize 10-DAB as a starting material to provide 7,10-di-O-alkyl-10-DAB via derivatives of 10-DAB that possess either or both 1,3-dithian-2-yl and 1,3-dithiolan-2-yl moieties. For example, Method A includes the conversion of 10-DAB to 1,3-dithian-2-yl or 1,3-dithiolan-2-yl derivatives XIVa, XIVb or XIVc which can be hydrodesulfurized to provide 7,10-di-O-methyl-10-DAB (XVa), that can be further converted to cabazitaxel (FIG. 7). Similarly, Method B includes the conversion of 10-DAB to XVIIa, which is then converted into XVIIIa and then XIXa (FIG. 8). Reaction of XIXa with 1,3-dithiolane derivatives or 1,3-dithiane derivatives provides 1,3-dithiolan-2-yl derivatives or 1,3-dithian-2-yl derivatives XVIa, XVIb or XVIc, which are converted to XVa via hydrodesulfurization. As in method A, XVa can be converted into cabazitaxel.

In Method A' and Method B', the C13-O-side chain is already attached to the 10-DAB skeleton prior to the hydrodesulfurization step. In Method A' (FIG. 9), for example, 10-DAB is converted into 1,3-dithian-2-yl or 1,3-dithiolan-2-yl derivatives XIVa, XIVb or XIVc as in Method A. However, the side chain (i.e., the (2R,3S)-N-t-butoxycarbonyl-3-phenylisoserinoyl radical) is installed to provide 1,3-dithian-2-yl or 1,3-dithiolan-2-yl derivatives XIVa', XIVb' or XIVc' prior to hydrodesulfurization. These compounds are directly hydrodesulfurized to provide XVa' which can be converted to cabazitaxel. Alternatively the 1,3-dithian-2-yl or 1,3-dithiolan-2-yl derivatives XIVa', XIVb' or XIVc' can be prepared by conversion of 10-DAB to XX as per methods known in the art (U.S. Pat. No. 5,847,170/WO 199533737 A1). In Method B' (FIG. 10), for example, 10-DAB is converted into XVIIa and then into XVIIIa. The side chain (i.e., the (2R,3S)-N-t-butoxycarbonyl-3-phenylisoserinoyl radical) is installed to provide XVIIIa' which is converted into XIXa' and then into 1,3-dithian-2-yl or 1,3-dithiolan-2-yl derivatives XVIa', XVIb' or XVIc' and these compounds are directly hydrodesulfurized to provide XVa' which can be converted to cabazitaxel.

Method A

Figure 11:
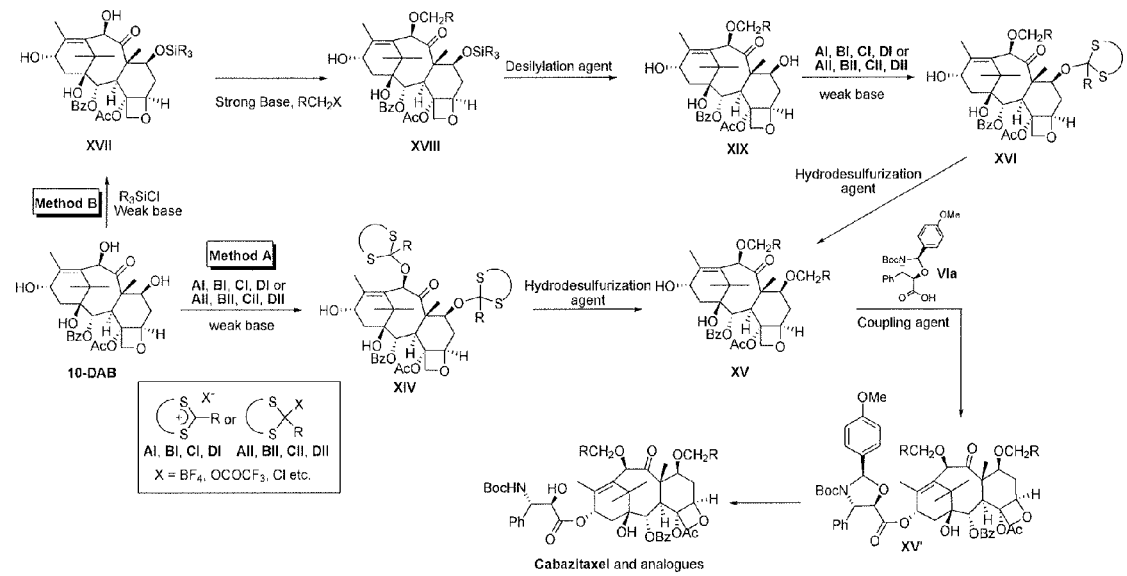
FIG. 11 shows the synthetic relationship between two methods (A and B) used to convert 7,10-di-O-alkyl-10-DAB (XV) to cabazitaxel.
Figure 12:
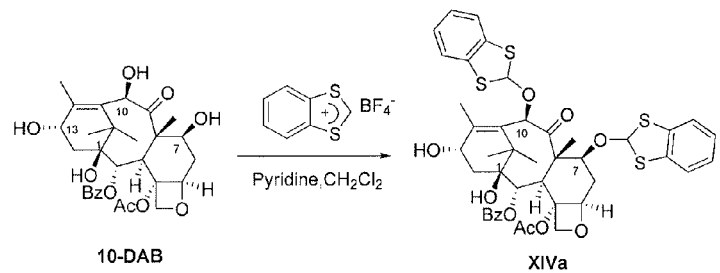
FIG. 12 shows the synthetic scheme for the preparation of XIVa.

C7-OH and C10-OH of 10-DAB are converted in one-step and in one-pot (FIG. 4) to their 1,3-dithiolane or 1,3-dithiane derivatives XIV via reaction with 1,3-dithian-2-ylium salts (AI), 1,3-dithiolan-2-ylium salts (BI), 1,3-dithiolium salts (CI), 1,3-benzodithiolium salts (DI), or alternatively with 1,3-dithiane derivatives (AII) or 1,3-dithiolane derivatives (BII)/(CII)/(DII) that possess a leaving group, X, at the C2 position in the presence of a weak base. Subsequently, XIV is treated with Raney Nickel, preferably but not essentially in a hydrogen atmosphere, or with other hydrodesulfurization agents to afford the desired 7,10-di-O-alkyl-10-DAB (XV). In some embodiments, trialkyltin hydrides such as $Bu_3SnH$ or trialkylgermanium hydrides such as $Bu_3GeH$ can be used as hydrodesulfurization agents with radical initiators such as 2,2'-azobis(2-methylpropionitrile) (AIBN), triethylborane or others. In some embodiments, $[NiCl_2]6H_2O$ in the presence of $NaBH_4$, optionally in the presence of reducing agents including hydrides or in the presence of hydrogen, can used as hydrodesulfurization agents. Still other reagents for conversion of XIV to XV are known in the art (See, Larock, R C. *Comprehensive Organic Transformations*. Weinheim: Wiley-VCH, 1999). XV is then coupled with side chain carboxylic acid VI using known conditions, to provide the corresponding ester product XV'. Coupling agents for the ester formation may include, but are not limited to, carbodiimides, carbonyl diimidazole (Arrieta, A. et al. *Synth Comm*. 1983, 13, 471). Removal of the oxazolidine protecting group from the side chain of XV' using conditions known in the art furnishes cabazitaxel or cabazitaxel analogues (see full synthetic route for Method A in FIG. 11).

Figure 3:
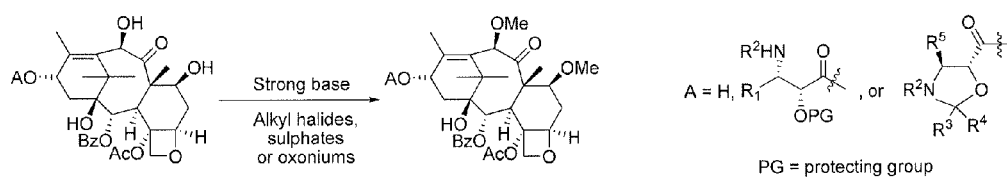
FIG. 3 shows the chemistry employed in the examples of U.S. Pat. No. 5,962,705.

Method A provides advantages for the synthesis of cabazitaxel and its analogues as compared to other known methods. For example, the method of U.S. Pat. No. 5,962,705 (FIG. 3) requires the use of strong bases, such as KH, that can lead to the formation of the undesired 7-epimer. Method A of the present invention, on the other hand, avoids epimerization of the C7-O position during the double alkylation of 10-DAB, due to the use of weak bases in the C7-O and C10-O functionalization step. The weak bases of the present invention are not strong enough to substantially deprotonate the hydroxyl groups of 10-DAB or its derivatives. Moreover, the method of U.S. Pat. No. 5,962,705 that uses KH requires a low temperature of –30° C. during the mixing of reagents and substrates (e.g., 10-DAB), whereas the equivalent step in the present invention can be conducted at ambient temperature (around 20-30° C.) without the need for cooling. The use of low reaction temperatures is also a disadvantage on manufacturing scales. For example, in a preferred embodiment of the present invention, 10-DAB is directly functionalized in one synthetic step by treatment with 1,3-benzodithiolium tetrafluoroborate in the presence of the weak base pyridine at room temperature in anhydrous dichloromethane. Following aqueous work-up and purification, XVa was isolated as a solid in 75% yield.

Furthermore, compared to the step-wise alkylation protocol described in U.S. Pat. No. 5,847,170 (FIG. 1), Method A completely avoids the use of protecting groups on the 10-DAB skeleton (i.e., the C7-O and C13-O hydroxyl groups) and avoids strong bases that can cause epimerization of the C7-OH hydroxyl group. Therefore, Method A is two synthetic steps shorter than the method shown in FIG. 1.

Figure 2:
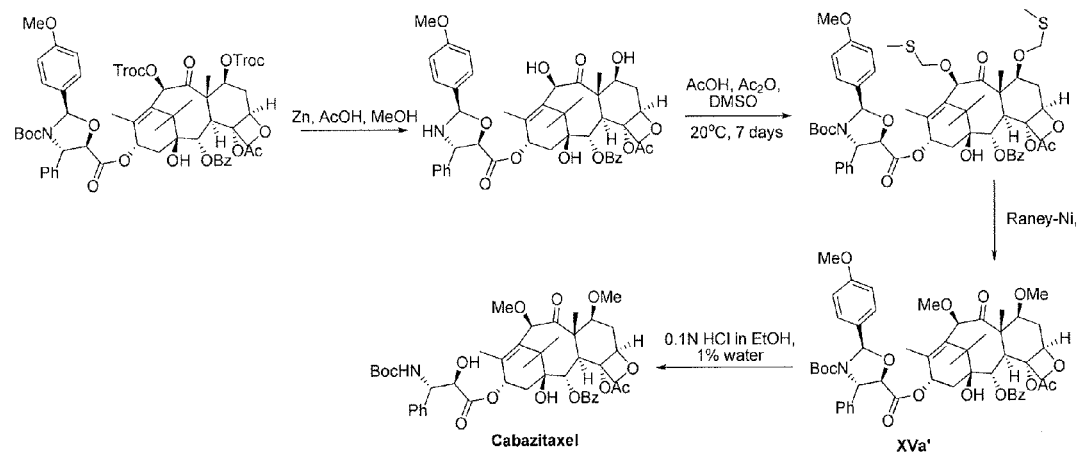
FIG. 2 shows the chemistry employed in the examples of U.S. Pat. No. 5,847,170.

Another advantage of Method A is that oxidation of the C13-OH moiety does not occur upon contacting 10-DAB with a weak base and a 1,3-dithiane, 1,3-dithiolane, or 1,3-dithiolium derivative. In contrast, the methodology disclosed in U.S. Pat. No. 5,847,170 (FIG. 2) leads to oxidation of the C13-OH to its corresponding ketone, due to the installation of methylthiomethyl (MTM) ether groups at C7-O and C10-O using $Ac_2O/DMSO$. Indeed, the inventors were surprised to discover that they could avoid the undesired oxidation of the C13-OH without the need for a protecting group by the synthesis of 1,3-dithiolan-2-yl or 1,3-dithian-2-yl derivatives instead of methylthiomethyl ether groups. Otherwise, to avoid this undesired oxidation, the C13-OH must be protected or already be block by the protected side chain. Method A completely avoids the use of protecting groups on the 10-DAB skeleton.

In a preferred embodiment of Method A (FIG. 7) of the present invention, the 1,3-dithiolane XIVa derivative of 10-DAB is formed in one reaction step in good yield (about 75%), and is then used in the synthesis of cabazitaxel through its hydrodesulfurization to provide XVa in good yield (about 60% by HPLC assay) that preferably is not isolated but is processed into the next reaction step (coupling with VIa) to provide XVa' that is then deprotected to provide cabazitaxel. The synthesis step of XIVa involves the reaction of 10-DAB in one synthetic step with commercially available 1,3-benzodithiolium tetrafluoroborate in the presence of the weak base in an organic solvent at ambient temperature. Preferably about 3 molar equivalents of 1,3-benzodithiolium tetrafluoroborate are used with respect to 10-DAB. If too little 1,3-benzodithiolium tetrafluoroborate is used, incomplete reaction occurs, and if too much is used, side products are formed. Useful solvents for this synthetic step include chlorinated solvents such dichloromethane (DCM), and non-chlorinated solvents including THF, acetonitrile, acetone and pyridine, or mixtures thereof. The use of dichloromethane can lead to particularly advantageous reaction rates. Other solvents can also be useful in the methods of the invention. Preferred temperatures include temperatures in the range of 10° C. to 35° C., such as ambient temperature. The weak bases include nitrogen containing bases such as pyridine, 2,6-lutidine, triethylamine, N,N-diisopropylethylamine. It is preferred that the reaction is conducted in the absence of moisture. Following aqueous work-up the product mixture can be purified and isolated in good yields (about 75% isolated yield) by known methods such as recrystallization or chromatography. Alternatively, the material can be used in the next step without purification.

The hydrodesulfurization of XIVa is preferably conducted in the presence of a nickel-containing reagent such as Raney Nickel under a pressurized atmosphere of hydrogen gas in an organic solvent at ambient temperatures or above. Preferably when Raney Nickel is used, the reagent is freshly prepared by digesting a 50/50 aluminum-nickel alloy with NaOH followed by neutralization and washing so that it is sufficiently activated (*Organic Syntheses, Coll.* 1955, 3, 176; *Organic Syntheses, Coll.* 1949, 9, 24). When the Raney Nickel is not sufficiently active the hydrodesulfurization reaction can be slow and/or can terminate before completion of the reaction or might not work at all. The hydrodesulfurization can be conducted in a range of solvents including ethanol (EtOH), n-butanol (n-BuOH), ethylene glycol, ethyl acetate (EtOAc), tetrahydrofuran (THF), 1,4-dioxane, acetonitrile (MeCN), dimethylformamide (DMF), N-methyl-2-pyrrolidone (NMP), 1,3-dimethyl-3,4,5,6-tetrahydro-2(1H)-pyrimidinone (DMPU), or mixtures thereof. DMF was found to be particularly useful in the hydrodesulfurization of XIVa.

Although the hydrodesulfurization reaction can be conducted in the absence of hydrogen gas, or in the presence of hydrogen gas at atmospheric pressure, it is preferred that the reaction is conducted under a pressurized atmosphere of hydrogen gas. In some embodiments, the hydrodesulfurization is conducted under a pressurized atmosphere of hydrogen gas at from about 20 psi to about 200 psi. In some embodiments, the hydrodesulfurization is conducted under a pressurized atmosphere of hydrogen gas at from about 50 psi to about 160 psi, or higher. The reaction can be slower at lower pressures. It is preferred that the hydrodesulfurization reaction of XIVa is conducted at ambient temperature or above. In some embodiments, the hydrodesulfurization is conducted at a temperature of from about 20° C. to about 70° C. In some embodiments, the hydrodesulfurization is conducted at about 50° C. Temperatures greater than ambient temperature lead to faster conversion of XIVa to XVa. Reaction monitoring of the hydrodesulfurization step by HPLC analysis indicates that when the preferred reaction conditions are used, the reaction is clean and fast. The reaction reaches completion within several hours when freshly activated Raney Nickel is used. The major reaction product XVa was formed in about 60% yield as determined by HPLC assay. Smaller amounts of the 10-deoxy derivative were formed.

Use of the hydrodesulfurization product mixture in the subsequent step without isolation and purification of XVa can lead to reduced losses in yield. That is, isolation and purification of XVa is less preferred from an efficiency point of view. For example, after the hydrodesulfurization reaction was complete as judged by HPLC analysis, the product mixture was directly filtered through a pad of an inert solid filter aid such as diatomaceous earth and washed with an organic solvent, such as ethyl acetate. A solvent capable of removing water by azeotropic distillation, such as 2-methyltetrahydrofuran or toluene, was added and the mixture was distilled to remove moisture. Following dilution with the solvent required for the next step, coupling of the thus obtained crude XVa with VIa can be directly conducted using known methods. The protecting group on the side chain of the product XVa' can then be deprotected, using known methods to provide cabazitaxel.

Method A'

The present invention also provides Method A' (FIG. 4) that is similar to Method A, with the key difference being that the protected side chain at C13-O is already attached to the 10-DAB skeleton prior to the hydrodesulfurization of the 1,3-dithiolan-2-yl groups installed at C7-O and C10-O of XIV'. The 1,3-dithiane and 1,3-dithiolane intermediate derivatives XIVa', XIVb' or XIVc' (FIG. 9) can be prepared from XIVa, XIVb or XIVc as described here, or can be prepared from XX (which is prepared using methods described in U.S. Pat. No. 5,847,170 and WO 1995/33737) in the same way that XIVa is prepared from 10-DAB. That is, starting with 10-DAB as the starting material, the order of the installation of the 1,3-dithiolan-2-yl or 1,3-dithian-2-yl moiety groups and the side chain is interchangeable to give the key intermediate XIV' (i.e., 10-DAB to XX and then to XIV', or 10-DAB to XIV and then to XIV').

For example, XIVa' is prepared from XIVa in high yield (96%) by coupling with VIa and a coupling agent, such as dicyclohexylcarbodiimide (DCC), according to known methods.

Alternatively, treatment of XX with a molar excess of 1,3-benzodithiolium tetrafluoroborate (DIa), 1,3-dithiolan-2-ylium trifluoroacetate (BIa), or 1,3-dithian-2-ylium trifluoroacetate (AIa) in the presence of the weak base in an organic solvent at ambient temperature provides XIVa', XIVb' or XIVc' in one synthetic step. In preferred embodiments, solvents for this synthetic step include chlorinated solvents such dichloromethane (DCM), and non-chlorinated solvents including THF, acetonitrile, acetone and pyridine, or mixtures thereof. Preferred temperatures include temperatures in the range of 10° C. to 35° C., such as ambient temperature. The weak bases include nitrogen containing bases such as pyridine, 2,6-lutidine, triethylamine, N,N-diisopropylethylamine. It is preferred that the reaction is conducted in the absence of moisture. For example, treatment of XX with a molar excess of 1,3-dithiolan-2-ylium trifluoroacetate (BIa) in THF as solvent in the presence of 2,6-lutidine at ambient temperature followed by an aqueous work-up and purification provides XIVb' in 90% yield. Those of skill in the art will know that 1,3-benzodithiolium, 1,3-dithiolium and 1,3-dithian-2-ylium salts are relatively reactive compounds and are liable to undergo auto-decomposition and decomposition in the presence of moisture and other impurities and that the selection of the most appropriate conditions can be found for each specific application by screening of reaction solvents, reaction temperatures, solute concentration, anionic counter ion of the salt and reaction bases.

XIV' can be converted into cabazitaxel in one-step, or in two steps via XVa'. The hydrodesulfurization of XIV' is similar to that for XIV of Method A and is preferably conducted in the presence of a nickel-containing reagent such as Raney Nickel under a pressurized atmosphere of hydrogen gas in an organic solvent at ambient temperatures or above. Preferably when Raney Nickel is used, the reagent is freshly prepared so that it is sufficiently active. The hydrodesulfurization can be conducted in a range of solvents including ethanol (EtOH), n-butanol (n-BuOH), ethylene glycol, ethyl acetate (EtOAc), tetrahydrofuran (THF), 1,4-dioxane, acetonitrile (MeCN), dimethylformamide (DMF), N-methyl-2-pyrrolidone (NMP), 1,3-dimethyl-3,4,5,6-tetrahydro-2(1H)-pyrimidinone (DMPU), or mixtures thereof. DMF was found to be particularly useful for the hydrodesulfurization of XIV'. Although the hydrodesulfurization reaction can be conducted in the absence of hydrogen gas, or in the presence of hydrogen gas at atmospheric pressure, it is preferred that the reaction is conducted under a pressurized atmosphere of hydrogen gas, preferably at 50 psi to 160 psi, or higher. It is preferred that the hydrodesulfurization reaction of XIV' is conducted at ambient temperature or above, preferably at about 50° C. Temperatures greater than ambient temperature can lead to faster conversion of XIV' to XVa'. Reaction monitoring of the hydrodesulfurization step by HPLC analysis indicates the major reaction product being is XVa' formed in about 50-60% yield as determined by HPLC assay, and a smaller amount of the 10-deoxy derivative. For example, hydrodesulfurization XIVa' in DMF in the presence of a suspension of Raney Nickel at 50° C. under an atmosphere of hydrogen gas at a pressure of 160 psi provided a 59% assay yield of XVa'. Purified XVa' was isolated in 51% yield.

In some instances, HPLC analysis of the hydrodesulfurization reaction of XIVa' indicated that XVa' was formed along with some cabazitaxel in small amounts. This was due to removal of the anisylidene protecting group of the side chain via hydrogenolysis. Those of skill in the art will recognize that cabazitaxel can be obtained as the major reaction product by appropriate optimization of the hydrodesulfurization reaction of 1,3-dithiolan-2-yl and 1,3-dithian-2-yl derivatives XIV'. Thus, one advantage of Method A' is that both the 1,3-dithiolan-2-yl or 1,3-dithian-2-yl groups and the side chain protecting group (an N,O-anisylidene acetal) of XIV' can be removed in one-step and one-pot to provide cabazitaxel or its analogues.

Method B

In another aspect of the invention, Method B can be used to prepare cabazitaxel. In Method B (FIG. 11), C7-OH of 10-DAB is selectively silylated (e.g., $SiR_3$=$SiEt_3$; TES (triethylsilyl)) to provide XVII. In some embodiments, the C7-OH group can be selectively protected using other strategies that are known in the art (Greene and Wuts, *Protective Groups in Organic Synthesis*. New York: John Wiley & Sons, Inc., 1999). In some embodiments, the C7-OH group can be selectively protected, without substantial concomitant protection of C10-OH and C13-OH, at not more than 0° C., preferably at not more than −10° C. XVII is subsequently alkylated at C10-OH using a strong base (e.g., LiHMDS) and an alkyl halide, or other alkylating agent, such as dialkyl sulfate, trialkyl oxonium salt or alkyl sulfonate, to provide XVIII. In this reaction the use of a strong base is applicable because C7-OH was protected as a silyl ether. Subsequent deprotection of the C7-O silyl group gives XIX which is then reacted with 1,3-dithian-2-ylium salts (AI), or 1,3-dithiolan-2-ylium salts (BI), or 1,3-dithiolium salts (CI), or 1,3-benzodithiolium salts (DI), or alternatively with 1,3-dithiane derivatives (AII) or 1,3-dithiolane derivatives (BII)/(CII)/(DII) in the presence of a weak base to provide 7-O-(1,3-dithiolan-2-yl) or 7-O-(1,3-dithian-2-yl) derivatives XVI, which is hydrodesulfurized to provide XV as described in Method A. The key intermediate XV is then converted to cabazitaxel or its analogues as described in Method A. In preferred embodiments, Method B comprises the conversion of 10-DAB to XVIIa to XVIIIa to XIXa to XVIa, XVIb or XVIc to XVa to XVa' to cabazitaxel (FIG. 8). In more preferred embodiments, XVIa is preferred over XVIb and XVIc.

One of the advantageous of Method B is that it does not require protection at C13-O. Thus, it is more atom economical compared with U.S. Pat. No. 5,847,170. Further, Method B can prevent epimerization at C7-OH because XVI is synthesized under mild conditions without a strong base.

Method B'

Method B' is a variation of Method B (FIG. 5). In preferred embodiments of Method B' (FIG. 10), 10-DAB is converted into XVIIa and then into XVIIIa. The side chain (i.e., the (2R,3S)-N-t-butoxycarbonyl-3-phenylisoserinoyl radical) is installed to provide XVIIIa' which is converted into XIXa' and then into 1,3-dithian-2-yl or 1,3-dithiolan-2-yl derivatives XVIa', XVIb' or XVIc' and these compounds are directly hydrodesulfurized to provide XVa'. The XVa' of this method can be converted to cabazitaxel as in Method A, Method A' and Method B. As for Method A', one advantage of Method B' is that both the 1,3-dithiolan-2-yl or 1,3-dithian-2-yl groups and the side chain protecting groups can be removed in one-step and one-pot by hydrodesulfurized and acetal hydrogenolysis. That is, under the appropriate conditions XVI' can be converted to cabazitaxel in one step.

Features that characterize the present invention are the novelty of specific molecules XIVa, XIVb, XIVc, XIVa', XIVb', XIVc', XVIa. Still other features and advantages reside in the use of 1,3-dithian-2-yl and 1,3-dithiolan-2-yl moieties as latent methyl groups in the synthesis of alkylated derivatives of 10-DAB, including cabazitaxel.

IV. Examples

The following examples are provided to further illustrate, but not to limit, this invention.

The symbols, conventions and abbreviations used in the in above specification and in the following examples are consistent with those used in the contemporary scientific literature, for example, JOC—the Journal of Organic Chemistry.

t-Bu—tert-butyl
Me—methyl
Et—ethyl
Pr—propyl
Ph—phenyl ($C_6H_5$)
$Et_2O$—diethyl ether
g—gram(s)
mg—milligram(s)
L—liter(s)
mL—milliliter(s)
m.p.—melting point
TBS—tert-butyldimethylsilyl
TBSCl—tert-butyldimethylsilyl chloride
M—molarity
N—normality
NMR—nuclear magnetic resonance
MHz—megahertz
mol—moles
mmol—millimoles
min—minutes
h—hours
TLC—thin layer chromatography
TES—triethylsilyl
TESCl—triethylsilyl chloride
TBAF—tetrabutylammonium fluoride
$R_f$—retention time
Raney Nickel—a nickel-based catalyst prepared from Ni/Al alloy
MeOH—methanol
2-Me-THF—2-methyltetrahydrofuran
MTBE—methyl tert-butyl ether
LiHMDS—lithium bis(trimethylsilyl)amide
PrOH—isopropanol PhMe—toluene
Pd/C—palladium on carbon
brine—saturated aqueous sodium chloride solution
AcOH—acetic acid
atm—atmosphere
TFA—trifluoroacetic acid
THF—tetrahydrofuran
NMP—N-methylpyrrolidinone
DMSO—dimethylsulfoxide
EtOAc—ethyl acetate
DCC—dicyclohexylcarbodiimide
DCM—dichloromethane
DCE—dichloroethane
DMAP—N,N-dimethyl-4-aminopyridine
DMF—N,N-dimethylformamide
atm—atmosphere
HPLC—high performance liquid chromatography
HRMS—high resolution mass spectrometry
psi—pounds per square inch
10-DAB—10-deacetylbaccatin III
v/v—volume per volume Example 1

Preparation of Dithiolane and Dithiane Derivatives of 10-DAB

Preparation of 7,10-di-O-1,3-benzodithiolan-2-yl-10-DAB (XIVa)

Figure 13:
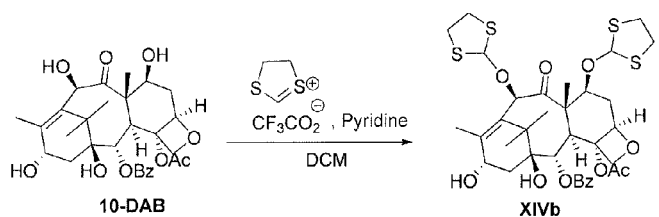
FIG. 13 shows the synthetic scheme for the preparation of XIVb from 10-DAB.

XIVa was prepared as shown in FIG. 13. To a suspension of 10-DAB (8.6 g, 15.8 mmol) at room temperature in anhydrous DCM (86 mL; water content ≤35 ppm (Karl Fischer analysis)) was added 1,3-benzodithiolium tetrafluoroborate (11.4 g, 47.5 mmol) and anhydrous pyridine (7.7 mL, 94.8 mmol; water content ≤35 ppm (Karl Fischer analysis)). The resulting mixture was stirred at room temperature for 21 h. After the reaction was completed (10-DAB was ≤0.5% by HPLC area %), triethylamine (5.5 mL, 39.5 mmol) was added and the resulting solution was stirred for an additional 15 min at room temperature. The reaction mixture was washed twice with 1 M HCl (86 mL, each) and then NaHCO₃ (86 mL), dried over MgSO₄, filtered and concentrated under reduced pressure (200-300 torr) until the volume reached about 4 volume of the original amount (54 mL). The mixture was washed with H₂O (86 mL) and concentrated under reduced pressure (200-300 torr). The residue was chromatographed on a column of silica gel eluting with n-heptane/EtOAc (1.5:1) to provide XIVa (10.4 g, 75%). $R_f$=0.65 (TLC, eluent: EtOAc/n-heptane (2/1, v/v). m.p. 165-170° C.; IR (KBr) 3534, 3058, 2946, 1717 cm$^{-1}$; $[\alpha]_{21}^D$=−91 (c=0.5; methanol); $^1$H NMR (400 MHz, CDCl₃) δ 8.02 (d, J=8.4 Hz, 2H), 7.61-7.58 (m, 1H), 7.48-7.46 (m, 2H), 7.41-7.40 (m, 6H), 7.15-7.13 (m, 4H), 6.61 (s, 1H), 6.27 (s, 1H), 5.56 (d, J=7.2 Hz, 1H), 5.42 (s, 1H), 4.90 (d, J=8.0 Hz, 1H), 4.80 (m, 1H), 4.50 (dd, J=10.8, 6.8 Hz, 1H), 4.29 (d, J=8.4, 1H), 4.13 (d, J=8.4, 1H), 3.86 (d, J=6.8 Hz, 1H), 2.66 (m, 1H), 2.28 (s, 3H), 2.25 (m, 2H), 2.21 (s, 3H), 1.71 (s, 3H), 1.09 (s, 3H), 0.96 (s, 3H); $^{13}$C NMR (100 MHz, CDCl₃) δ 203.9, 170.7, 167.0, 142.6, 136.6, 135.6, 135.1, 134.7, 133.6, 133.1, 130.1, 129.3, 128.6, 126.0, 125.9, 125.3, 125.1, 122.6, 122.6, 122.3, 89.7, 88.2, 83.6, 80.7, 80.3, 78.7, 77.1, 76.5, 74.3, 68.0, 57.0, 47.6, 42.7, 38.3, 33.3, 26.7, 22.7, 19.9, 15.3, 10.8; HRMS calculated for $C_{43}H_{44}O_{10}S_4$ was 848.1817, and found: 848.1786.

Preparation of 1,3-dithiolan-2-ylium trifluoroacetate (BIa)

To a stirred of solution of 1,3-dithiolane (4.8 g, 45 mmol) in methanol (225 mL) at 0° C. was added dropwise a solution of (9.6 g, 45 mmol) sodium periodate in water (70 mL). After stirring overnight the precipitated solids were removed by filtration and the filtrate was evaporated. The residue was dissolved in dichloromethane, dried over MgSO₄ and the solvent was evaporated to dryness. The product was purified by column chromatography over silica gel and eluted with 2:1 EtOAc/n-heptane to obtain 1,3-dithiolane-1-oxide (4 g) in 73% yield. A THF (40 mL) solution of the above prepared 1,3-dithiolane-1-oxide (2.8 g, 23 mmol) was treated with trifluoroacetic anhydride (3.2 mL, 23 mmol) furnishing 1,3-dithiolan-2-ylium trifluoroacetate salt (BIa) (23 mmol).

Preparation of 7,10-di-O-1,3-dithian-2-yl-10-DAB (XIVb)

XIVb was prepared as shown in FIG. 13. To a suspension of 10-DAB (100 mg, 0.18 mmol) in anhydrous DCM (2 mL) was added 1,3-dithiolan-2-ylium trifluoroacetate (BIa) (128 mg, 0.55 mmol) and anhydrous pyridine (150 µL, 1.8 mmol). The resulting mixture was stirred at ambient temperature. After the reaction was complete, triethylamine (204 µL, 1.8 mmol) was added and the resulting solution was stirred for an additional 15 min. The reaction mixture was washed with 1 M HCl (10 mL) and then water, dried over MgSO₄, filtered and concentrated under reduced pressure. The residue was chromatographed on a column of silica gel with THF/n-heptane (1:4) to provide XIVb as a white solid. $R_f$=0.7 (TLC, eluent: EtOAc/n-heptane (3/1, v/v). m.p. 189-194° C.; $[\alpha]_{20}^D$=−9.0 (c=1.0; methanol); $^1$H NMR (400 MHz, DMSO) δ 8.02 (d, J=7.6 Hz, 2H), 7.66 (t, J=7.6 Hz, 1H) (m, 1H), 7.56 (t, J=7.6 Hz, 2H), 6.46 (s, 1H), 6.19 (s, 1H), 5.40 (s, 1H), 5.39 (m, 1H), 5.35 (d, J=4.4 Hz, 1H), 4.94 (d, J=9.2 Hz, 1H), 4.68 (m, 1H), 4.48 (s, 1H), 4.09 (m, 1H), 4.04 (s, 2H), 3.75 (d, J=6.8 Hz, 1H), 3.40-3.20 (m, 8H), 2.87 (m, 1H), 2.20 (m, 2H), 2.08 (s, 3H), 1.54 (m, 1H), 1.54 (s, 3H), 0.95 (s, 3H), 0.93 (s, 3H); $^{13}$C NMR (100 MHz, DMSO) δ 203.9, 169.7, 165.2, 146.1, 133.2, 130.6, 130.1, 129.5, 128.7, 89.3, 89.2, 82.7, 81.0, 79.8, 76.7, 75.8, 75.3, 74.3, 66.0, 56.5, 46.6, 42.4, 39.0, 38.2, 37.9, 37.8, 32.0, 26.4, 22.3, 20.2, 15.2, 10.5; HRMS calculated for $C_{35}H_{44}O_{10}S_4$ was 752.1817 and found 752.1763.

Preparation of XIVb

Figure 14:
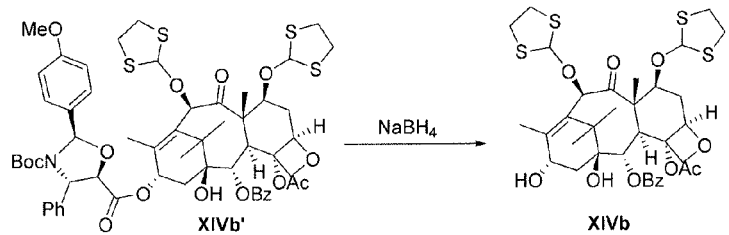
FIG. 14 shows the synthetic scheme for the preparation of XIVb from XIVb'.

XIVb was also synthesized from XIVb' as shown in FIG. 14. To a solution of XIVb' (5.2 g, 4.6 mmol) in a mixture of THF (40 mL) and MeOH (80 mL) was added NaBH₄ (1.0 g, 27.5 mmol). The resulting mixture was stirred at ambient temperature for 3 h. After the reaction was complete as determined by TLC analysis, water (10 mL) was added and the resulting solution was stirred for an additional 15 min. The organic phase was concentrated until 3 volumes remained and was then extracted with EtOAc (100 mL). The organic layer was dried over MgSO₄, filtered and concentrated under reduced pressure. The residue was chromatographed on a column of silica gel eluting with EtOAc/n-heptane (1:1) to furnish XIVb (3.5 g, 80%) as a white solid.

Preparation of 1,3-dithian-2-ylium trifluoroacetate (AIa)

To a stirred solution of 1,3-dithiane (6.1 g, 50 mmol) in methanol (280 mL) at 0° C. was added dropwise a solution of sodium periodate (10.8 g, 50 mmol) in water (85 mL). After stirring overnight the precipitated solids were removed by filtration and the filtrate was evaporated. The residue was dissolved in dichloromethane, dried over MgSO₄ and the solvent was evaporated to dryness. The resultant oil was column purified over silica gel eluting with 5% MeOH/DCM to provide 1,3-dithiane-1-oxide (6.5 g) in 94% yield. A THF (10 mL) solution of 1,3-dithiane-1-oxide (1 g, 7.3 mmol) was treated with trifluoroacetic anhydride (1 mL, 7.3 mmol) providing a solution of 1,3-dithian-2-ylium trifluoroacetate (AIa) (7.3 mmol).

Preparation of XIVc

Figure 15:
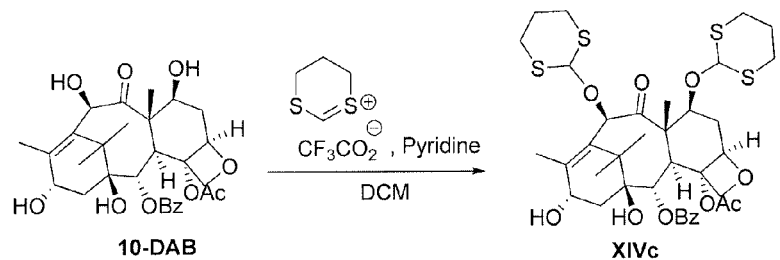
FIG. 15 shows the synthetic scheme for the preparation of XIVc.

XIVc was prepared as shown in FIG. 15. To a suspension of 10-DAB (100 mg, 0.18 mmol) in anhydrous DCM (2 mL) was added 1,3-dithian-2-ylium trifluoroacetate (AIa) (128 mg, 0.55 mmol) and anhydrous pyridine (150 μL, 1.8 mmol). The resulting mixture was stirred at ambient temperature. After the reaction was complete, triethylamine (204 μL, 1.8 mmol) was added and the resulting solution was stirred for an additional 15 min. The reaction mixture was washed with 1 M HCl (10 mL) and then washed with water, dried over $MgSO_4$, filtered and concentrated under reduced pressure. The residue was chromatographed on a column of silica gel with THF/n-heptane (1:4) to provide XIVc. $^1$H NMR (400 MHz, $CDCl_3$) δ 8.02 (dd, J=7.2, 8.4 Hz, 2H), 7.63-7.61 (m, 1H), 7.49 (dd, J=15.6, 8 Hz, 2H), 6.99 (s, 2H), 5.67 (d, J=8.0 Hz, 1H), 5.53 (s, 1H), 5.48 (s, 1H), 5.00-4.98 (m, 1H), 4.97-4.96 (m, 1H), 4.32 (d, J=8.0 Hz, 2H), 4.17 (d, J=10.4 Hz, 1H), 3.96 (d, J=6.8 Hz, 1H), 3.76-3.75 (m, 1H), 3.51-3.40 (m, 2H), 2.61-2.56 (m, 3H), 2.31-2.29 (m, 5H), 2.20-2.06 (m, 6H), 1.87-1.85 (m, 2H), 1.70-1.68 (m, 6H), 1.45 (s, 3H), 1.28-1.26 (m, 5H), 1.14-1.11 (m, 4H), 0.90-0.88 (m, 2H).

Figure 16:
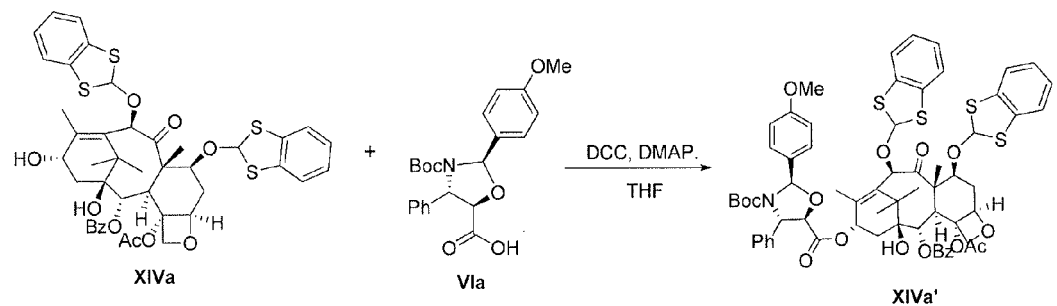
FIG. 16 shows the synthetic scheme for the preparation of XIVa' from XIVa.

Preparation of (2α,5β,7β,10β,13α)-4-acetoxy-13-{(2R,4S,5R)-3-tert-butoxycarbonyl-2-(4-methoxyphenyl)-4-phenyl-1,3-oxazolidine-5-carboxy}-1-hydroxy-7,10-di-O-1,3-benzodithiolan-2-yl-9-oxo-5,20-epoxy-tax-11-en-2-yl benzoate (XIVa') from XIVa XIVa' was prepared according to FIG. 16. To a THF (49 mL) solution of XIVa (4.9 g, 5.8 mmol), DMAP (141 mg, 1.2 mmol) and VIa (3.5 g, 8.7 mmol) was added dicyclohexylcarbodiimide (1.8 g, 8.7 mmol). The solution was stirred for 18 h at room temperature. After reaction was complete as determined by TLC analysis, the reaction was quenched with 1 M HCl (25 mL). The reaction mixture was filtered and washed with EtOAc (125 mL) and the organic layer was washed with $NaHCO_3$ (25 mL) and then with water (25 mL) and evaporated in vacuo to provide an oil (50-100 torr) that was purified by column chromatography eluting with EtOAc/n-heptane (1:3) to furnish XIVa' (6.8 g, 96%) as a white solid. $R_f$=0.42 (TLC, eluent: EtOAc/n-heptane (1/1, v/v). m.p. 167-170° C.; IR (KBr) 3479, 2931, 1716, 1612 $cm^{-1}$; $^1$H NMR (400 MHz, DMSO) δ 7.94 (d, J=7.2 Hz, 2H), 7.69-7.67 (m, 1H), 7.57 (t, J=9.5 Hz, 1H), 7.48-7.41 (m, 12H), 7.22-7.15 (m, 4H), 7.03-7.01 (m, 2H), 7.00 (s, 1H), 6.44 (m, 1H), 6.14 (s, 1H), 5.88 (m, 1H), 5.36 (d, J=6.8 Hz, 1H), 5.25 (s, 1H), 4.82 (d, J=10 Hz, 1H), 4.81 (s, 1H), 4.75 (m, 1H), 4.30-4.26 (m, 1H), 3.97 (s, 2H), 3.78 (s, 3H), 3.55 (d, J=8.0 Hz, 1H), 2.81-2.78 (m, 1H), 2.52-2.50 (m, 1H), 2.01-1.96 (m, 1H), 1.79 (m, 3H), 1.69-1.61 (m, 4H), 1.48 (s, 3H), 0.98 (s, 9H), 0.94 (s, 3H), 0.88 (s, 3H); $^{13}$C NMR (100 MHz, DMSO) δ 203.8, 170.4, 169.9, 156.6, 160.3, 139.7, 136.0, 135.9, 135.1, 134.9, 133.9, 133.5, 130.3, 130.0, 129.1, 129.0, 128.2, 126.3, 126.2, 123.0, 129.1, 129.0, 128.2, 126.3, 123.0, 122.9, 122.8, 114.0, 91.7, 89.6, 88.5, 83.1, 80.5, 80.1, 80.0, 77.1, 75.7, 74.5, 71.9, 56.6, 55.7, 46.3, 43.2, 40.6, 33.1, 31.7, 28.8, 27.9, 26.8, 22.6, 21.7, 21.5, 14.4, 14.0, 11.0; HRMS calculated for $C_{65}H_{67}NO_{15}S_4$ was 1229.3394, and found 1229.3271.

Preparation of XIVa' from XX

Figure 17:
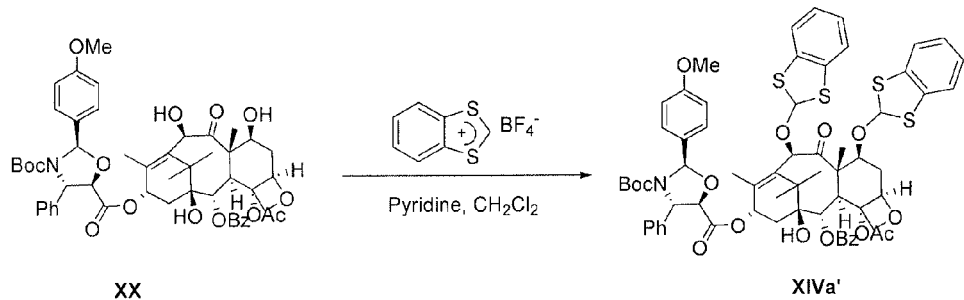
FIG. 17 shows the synthetic scheme for the preparation of XIVa' from XX.

IM14a' was prepared according to FIG. 17. To a suspension of XX (309 mg, 0.12 mmol; which is made as according to U.S. Pat. No. 5,847,170/WO 199533737 A1) in anhydrous DCM (3.0 mL) was added, 1,3-benzodithiolium tetrafluoroborate (261 mg, 1.09 mmol) and anhydrous pyridine (176 μL, 2.18 mmol). The reaction was stirred until it was complete (about 14 h), the mixture was diluted with DCM (10 mL) and triethylamine (380 μL, 1.8 mmol) was then stirred for an additional 15 minutes. The mixture was washed with 1 M HCl (10 mL) and then with water (5 mL), dried over $MgSO_4$, filtered and concentrated under reduced pressure. The residue was chromatographed over a column of silica gel eluting with n-heptane/EtOAc (2:1) to provide XIVa' (50 mg).

Preparation of XIVb'

Figure 18:
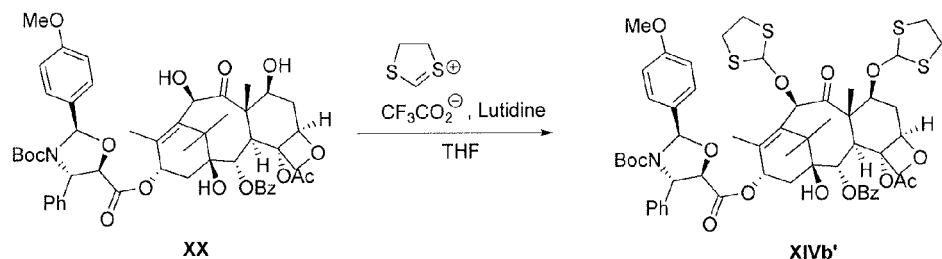
FIG. 18 shows the synthetic scheme for the preparation of XIVb'.

XIVb' was prepared according to FIG. 18. To a suspension of XX (5 g, 5.4 mmol; prepared according to U.S. Pat. No. 5,847,170/WO 199533737 A1) in THF (40 mL) was added 1,3-dithiolan-2-ylium trifluoroacetate (7.7 g, 23.2 mmol) and 2,6-lutidine (6.3 mL, 54 mmol). The resulting mixture was stirred at 10-25° C. and after the reaction was complete as determined by TLC analysis, water (10 mL) was added and the resulting solution was stirred for an additional 15 min. The reaction mixture was evaporated to remove the THF and was extracted with EtOAc (150 mL) and washed with 10% NaCl aqueous (40 mL) twice and then brine (20 mL), dried over $Na_2SO_4$, filtered and concentrated under reduced pressure. The residue was chromatographed on a column of silica gel with EtOAc/n-heptane (1:3) to provide XIVb' (5.5 g, 90%). $R_f$=0.2 (TLC, eluent: EtOAc/n-heptane (1/3, v/v); m.p. 184-200° C.; $[α]_{20}^D$=11.5 (c=1.0; methanol); $^1$H NMR (400 Hz, DMSO) δ 7.96 (dd, J=8.4, 7.2 Hz, 2H), 7.70 (dd, J=14.8, 7.2 Hz, 1H), 7.58 (dd, J=15.6, 8.0 Hz, 2H), 7.46 (m, 5H), 7.58 (dd, J=8.4, 7.2 Hz, 2H), 6.96 (d, J=7.2 Hz, 2H), 6.43 (s, 1H), 6.43 (m, 1H), 6.09 (s, 1H), 5.91 (m, 1H), 6.40 (d, J=6.8 Hz, 1H), 5.39 (m, 1H), 5.27 (s, 1H), 4.85-4.83 (m, 2H), 4.73 (s, 1H), 3.99-3.95 (m, 3H), 3.76 (s, 1H), 3.58 (d, J=7.2 Hz, 1H), 3.35-3.32 (m, 5H), 3.22 (m, 3H), 2.84-2.81 (m, 1H), 2.27-2.23 (m, 1H), 2.05-2.01 (m, 1H), 1.79 (s, 3H), 1.56 (s, 3H), 1.05 (s, 3H), 1.05-0.96 (m, 12H); $^{13}$C NMR (100 MHz, DMSO) δ 203.0, 170.4, 170.0, 165.6, 160.3, 140.4, 133.9, 133.2, 130.3, 130.1, 129.1, 129.0, 128.2, 127.3, 113.9, 91.7, 90.1, 89.7, 83.2, 80.7, 80.3, 80.0, 77.1, 76.0, 75.7, 74.7, 72.0, 56.9, 55.7, 46.5, 43.3, 40.6, 35.5, 32.4, 31.7, 27.9, 26.6, 21.8, 21.3, 13.9, 11.0; HRMS calculated for $C_{57}H_{67}NO_{15}S_4$ was 1133.3394, and found 1133.3344.

Preparation of XIVc'

Figure 19:
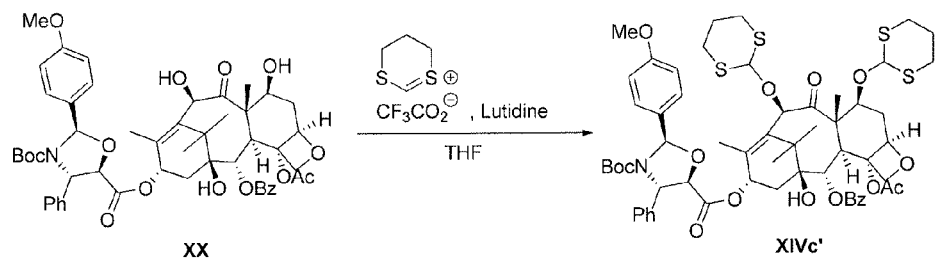
FIG. 19 shows the synthetic scheme for the preparation of XIVc'.

XIVc' was prepared according to FIG. 19. To a suspension of XX (1.6 g, 1.7 mmol) in THF (10 mL, 6 vol) was added 1,3-dithian-2-ylium trifluoroacetate (2.5 g, 7.3 mmol) and 2,6-lutidine (2 mL, 17 mmol). The resulting mixture was stirred at 10-25° C. After reaction was complete as determined by TLC analysis, water (10 mL) was added and the resulting solution was stirred for an additional 15 min. The reaction mixture was evaporated to remove the THF and was extracted with EtOAc (150 mL, 94 vol), washed twice with 10% NaCl aqueous (40 mL, each) and then with brine (20 mL, 13 vol), dried over $Na_2SO_4$, filtered and concentrated under reduced pressure. The residue was chromatographed on a column of silica gel with EtOAc/toluene (1:5) to provide XIVc' (0.232 g). $R_f$=0.2 (TLC, eluent: EtOAc/toluene (1/5, v/v); m.p. 178-189° C.; $^1$H NMR (400 MHz, DMSO) δ 7.98 (d, J=7.2 Hz, 2H), 7.70 (dd, J=14.8, 7.6 Hz, 1H), 7.58 (dd, J=15.2, 7.6 Hz, 2H), 7.45 (m, 5H), 6.96-6.94 (m, 5H), 6.43 (m, 1H), 5.89 (s, 1H), 5.46 (s, 1H), 5.39 (m, 5H), 5.34 (s, 1H), 5.27 (s, 1H), 4.84-4.82 (m, 2H), 4.72 (s, 1H), 4.15-4.12 (m, 1H), 4.00-3.97 (m, 2H), 3.75 (s, 3H), 3.64 (d, J=7.2 Hz, 1H), 3.20-3.18 (m, 1H), 3.07-2.98 (m, 3H), 2.76-2.64 (m, 5H), 2.32-2.28 (m, 1H), 2.15-1.95 (m, 6H), 1.81 (s, 3H), 1.72-1.61 (m, 2H), 1.59 (s, 3H), 1.46 (s, 3H), 1.08 (s, 6H), 0.98 (s, 6H); $^{13}$C NMR (100 MHz, DMSO) δ 203.9, 170.8, 170.4, 170.0, 165.6, 160.2, 151.3, 139.8, 133.9, 133.8, 130.4, 130.1, 129.4, 129.2, 129.0, 128.7, 128.3, 127.3, 113.9, 91.7, 83.3, 80.3, 80.0, 78.9, 77.8, 77.2, 76.7, 75.7, 74.8, 71.9, 63.1, 60.2, 57.3, 55.7, 46.4, 43.4, 35.7, 33.4, 27.9, 26.5, 25.6, 25.5, 25.3, 25.0, 24.9, 24.7, 21.8, 21.3, 21.2, 13.3, 11.2; HRMS calculated for $C_{59}H_{71}NO_{15}S_4$ was 1161.3707, and found 1161.3637.

Example 2

Preparation of 7,10-di-O-methyl derivatives of 10-DAB

Preparation of Raney Nickel

The Raney Nickel used in the experiments below was freshly-made by digesting the 50/50 aluminum-nickel alloy with NaOH followed by neutralization and washing: A solution of NaOH (63 g) in water (250 mL) was cooled in an ice bath to 0-10° and nickel-aluminum alloy (50 g of Fluka aluminum-nickel alloy: 50% Al basis, 50% Ni basis) was added to the solution, with stirring, in small portions at such a rate that the temperature did not rise above 25° C. The mixture was allowed to warm to room temperature and was stirred for 1 h. After the rate of evolution of hydrogen significantly reduced or ceased, the mixture was carefully and gradually warmed to about 50° C. and stirred for 1 h until the rate of evolution of hydrogen significantly reduced or ceased. The mixture was cooled to room temperature and the solids were allowed to settle and the majority of the liquid phase was decanted off. Water was added until the total volume of the mixture measured about 250 mL. The mixture was stirred for several minutes and then the solids were allowed to settle, and the liquid phase was decanted off. This stirring, settling and decanting procedure was repeated twice more. A solution of NaOH (8.0 g) in water (80 mL) was added to the mixture and the mixture was stirred for several minutes and was then allowed to settle. The liquid phase was decanted off. The solids were successively wash with water and until the washings were about neutral pH (pH=7~8) (500 mL each, 12 times). The solids were washed two times with 95% ethanol (250 mL each) and then two times with absolute ethanol (250 mL each). The solids are referred herein as Raney Nickel and were stored under absolute ethanol in a sealed flask and were typically used within several days of having been preferred.

Preparation of 7,10-di-O-methyl-10-DAB (XVa) from XIVa

Figure 20:
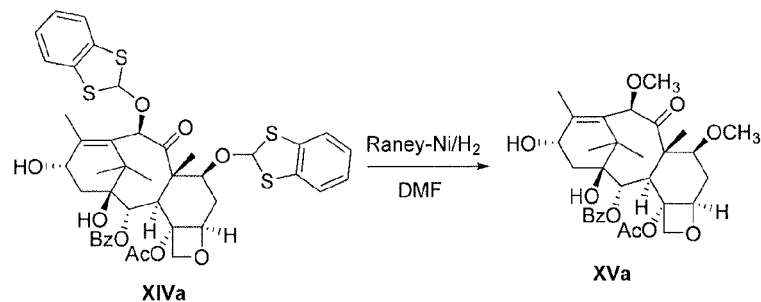
FIG. 20 shows the synthetic scheme for the preparation of XVa from XIVa.

XVa was prepared according to FIG. 20. A DMF (3 mL) solution of 7,10-di-O-1,3-benzodithiolan-2-yl-10-DAB (XIVa, 100 mg, 0.12 mmol) was hydrogenolysed in the presence of a suspension of Raney Nickel (approximately 2.1 g) under an atmosphere of 3.4 atm of hydrogen gas at ambient temperature for 15 hours. The mixture was filtered through a pad of diatomaceous earth and washed with EtOAc and this was evaporated to give an oil. The mixture dissolved in EtOAc, was washed three times with water and was evaporated to provide an oil that after purification by column chromatography (eluting with 1:1 n-heptane/EtOAc) provided XVa (27 mg, 42%). $R_f$=0.28 (EtOAc/n-heptane (2/1, v/v). m.p. 249-251° C.; IR (KBr) cm$^{-1}$; IR (KBr) 3553, 3435, 2945, 2893, 2827, 1705 cm-1; $[α]^{21}_D$=−59 (c=0.5; methanol); $^1$H NMR (400 MHz, DMSO) δ 8.02 (d, J=7.2 Hz, 2H), 7.68-7.65 (m, 1H), 7.57 (t, J=8 Hz, 2H), 5.39 (d, J=6.8 Hz, 1H), 5.31 (d, J=4.4 Hz, 1H), 4.98 (d, J=9.2 Hz, 1H) 4.75 (s, 1H), 4.66-4.65 (m, 1H), 4.40 (s, 1H), 4.06-4.01 (m, 2H), 3.83-3.79 (m, 1H), 3.75 (d, J=7.2 Hz, 1H), 3.30 (s, 3H), 3.22 (s, 3H), 2.69-2.65 (m, 1H), 2.21 (s, 3H), 2.20-2.17 (m, 2H), 1.98 (s, 3H), 1.52 (s, 3H), 1.52-1.46 (m, 1H), 0.91 (s, 6H); $^{13}$C NMR (100 MHz, DMSO) δ 205.9, 170.1, 165.7, 144.5, 133.7, 133.3, 130.7, 130.0, 129.1, 83.8, 83.3, 20.9, 80.6, 77.3, 75.8, 74.9, 66.6, 57.1, 56.9, 56.5, 47.5, 42.9, 40.6, 32.3, 27.4, 22.8, 21.0, 15.6, 10.5; HRMS calculated for $C_{31}H_{40}O_{10}$ was 572.2621, and found 572.2581.

Preparation of 7,10-di-O-methyl-10-DAB (XVa) from XIVb

Figure 21:
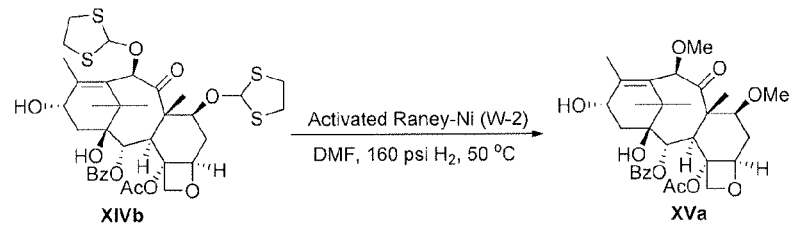
FIG. 21 shows the synthetic scheme for the preparation of XVa from XIVb.

XVa was prepared according to FIG. 21. A DMF (48 mL) solution of XIVb (4.8 g, 6.4 mmol) was hydrogenolysed in the presence of a suspension of Raney Nickel (approximately 75 g) under an atmosphere of hydrogen gas at 160 psi at 50° C. for 23 h. After the reaction was complete as determined by HPLC analysis, the product mixture was filtered through a pad of diatomaceous earth and washed with EtOAc (250 mL). HPLC analysis indicated a 49% purity (area %) of XVa and HPLC assay indicated a 43% yield of XVa (based on XIVb).

Preparation of 7,10-di-O-methyl-10-DAB (XVa) from XIVc

Figure 22:
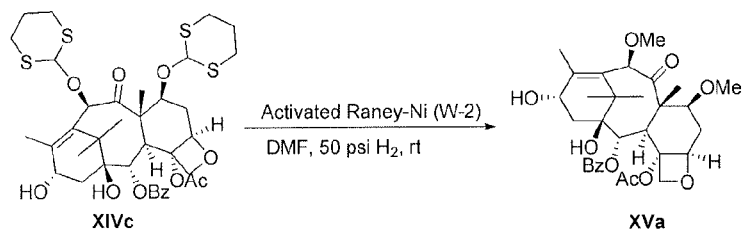
FIG. 22 shows the synthetic scheme for the preparation of XVa from XIVc.

XVa was prepared according to FIG. 22. A DMF (1 mL) solution of XIVc (10 mg, 0.01 mmol) was hydrogenolysed in the presence of a suspension of Raney Nickel (approximately 0.5 g) under an atmosphere of hydrogen gas at 3.4 atm at ambient temperature for 15 hours. The mixture was filtered through a pad of diatomaceous earth and washed with EtOAc and this was evaporated to give an oil that after purification by column chromatography (eluting with 1:1 n-heptane/EtOAc) provided XVa.

Preparation of 7,10-di-O-methyl-10-DAB (XVa) from XIVa and then conversion to (2α,5β,7β,10β, 13α)-4-acetoxy-13-{(2R,4S,5R)-3-tert-butoxycarbonyl-2-(4-methoxyphenyl)-4-phenyl-1,3-oxazolidine-5-carboxy}-1-hydroxy-7,10-dimethoxy-9-oxo-5,20-epoxy-tax-11-en-2-yl benzoate (XVa')

Figure 23:
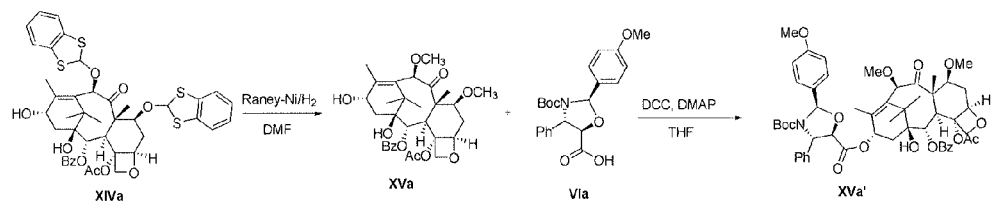
FIG. 23 shows the synthetic scheme for the preparation of XVa' from XIVa.

A DMF (50 mL) solution of XIVa (5 g, 5.9 mmol) was hydrogenolysed in the presence of a suspension of Raney Nickel (approximately 70 g) under an atmosphere of hydrogen gas at 160 psi and 50° C. for 24 h. After the reaction was complete as judged by HPLC analysis, the product mixture was filtered through a pad of diatomaceous earth and washed with EtOAc (250 mL). HPLC analysis indicated 62% purity of XVa and HPLC assay indicated a 57% yield of XVa. The crude XVa was dried by mixing with toluene and distillation of the toluene (100 mL each, three times) at NMT 50° C. under reduced pressure (30-50 torr) to azeotropically remove moisture. See FIG. 23.

To an anhydrous THF (50 mL; water content ≤200 ppm by Karl Fischer titration) solution of XVa was added VIa (6.1 g, 15.3 mmol), DMAP (143 mg, 1.2 mmol) and DCC (3.0 g, 14.8 mmol). The reaction was stirred at r.t. until the reaction was complete (about 2 h) as determined by HPLC analysis. 1 M HCl (10 mL) was added and the mixture was filtered and washed with EtOAc (100 mL). The filtrate was washed with NaHCO$_3$ (50 mL) and then twice with water (each 100 mL). The organic layer was evaporated under vacuum and the resulting oil was purified by column chromatography eluting with EtOAc/n-heptane (1.5:1) to furnish XVa' (2.88 g, 49% based on XIVa) as a white solid. $R_f$=0.59 (TLC, eluent: EtOAc/n-heptane (2/1, v/v); m.p. 219-221° C.; IR (KBr) 3421, 2985, 2937, 1754, 1708 cm$^{-1}$; $[\alpha]_{21}^D$=−23 (c=0.5; methanol); $^1$H NMR (400 Hz, MHz, CDCl$_3$) δ 8.04 (dd, J=8, 1.2 Hz, 2H), 7.65-7.61 (m, 1H), 7.52-7.44 (m, 9H), 6.93 (dd, J=6.8, 2.8 Hz, 2H), 6.40-6.39 (m, 1H), 6.16 (m, 1H), 5.60 (d, J=7.2 Hz, 1H), 5.44 (m, 1H), 4.91 (d, J=8.4 Hz, 1H), 4.72 (s, 1H), 4.59 (d, J=5.2 Hz, 1H), 4.24 (d, J=8.4 Hz, 1H), 4.10 (d, J=8.4 Hz, 1H), 3.85-3.80 (m, 4H), 3.74 (d, J=6.8 Hz, 1H), 3.42 (s, 3H), 3.29 (s, 3H), 2.70-2.63 (m, 1H), 2.11-2.05 (m, 2H), 1.83 (s, 3H), 1.78-1.59 (m, 2H), 1.63 (s, 3H), 1.59 (s, 3H), 1.22 (s, 3H), 1.18 (s, 3H), 1.07 (s, 9H); $^{13}$C NMR (100 Hz, MHz, CDCl$_3$) δ 204.8, 169.9, 169.5, 166.9, 160.4, 151.5, 139.0, 135.1, 133.7, 130.1, 129.0, 128.7, 128.6, 128.2, 126.6, 113.9, 92.6, 84.1, 82.4, 81.3, 80.6, 79.1, 74.7, 71.8, 63.7, 57.1, 57.0, 56.7, 55.3, 47.3, 43.2, 35.4, 34.0, 31.9, 27.8, 26.7, 21.6, 20.9, 13.9, 10.3; HRMS calculated for C$_{53}$H$_{53}$NO$_{15}$ was 953.4198, and found 953.4163.

Preparation of XVa' from XIVa'

Figure 24:
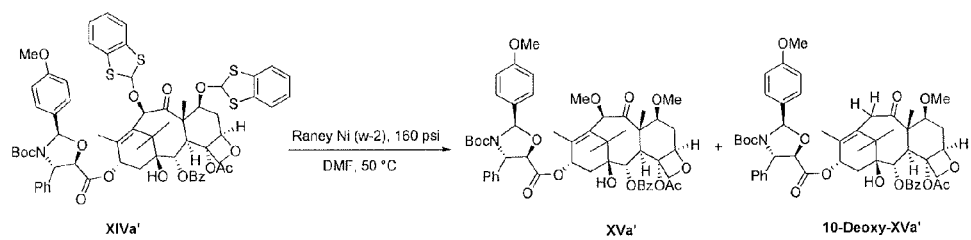
FIG. 24 shows the synthetic scheme for the preparation of XVa' from XIVa'.

XVa' was prepared according to FIG. 24. XIVa' (5 g, 4.1 mmol) in DMF (50 mL) was hydrogenolysed in the presence of a suspension of Raney Nickel (approximately 50 g) at 50° C. for 15 h under an atmosphere of hydrogen gas at 160 psi. The spent Raney Nickel was removed by filtration and an additional amount of Raney Nickel (approximately 25 g) was added, the vessel was repressurized with hydrogen gas and the hydrogenolysis was continued until completion (another 3 h), as determined by HPLC analysis. HPLC analysis of the product mixture showed 58 area % of XVa' and 18 area % of 10-Deoxy-XVa', which is a 3.2:1 ratio. The mixture was filtered through a pad of diatomaceous earth and washed with EtOAc (250 mL). HPLC assay analysis a 59% yield was obtained. The organic layer was evaporated under vacuum to provide an oil that was purified by column chromatography eluting with EtOAc/n-heptane (1:1.5) to furnish XVa' (2 g, 51%). 10-Deoxy-XVa' (970 mg, 26%) was separated isolated as another fraction as a white solid.

Preparation of XVa' from XIVb'

Figure 25:
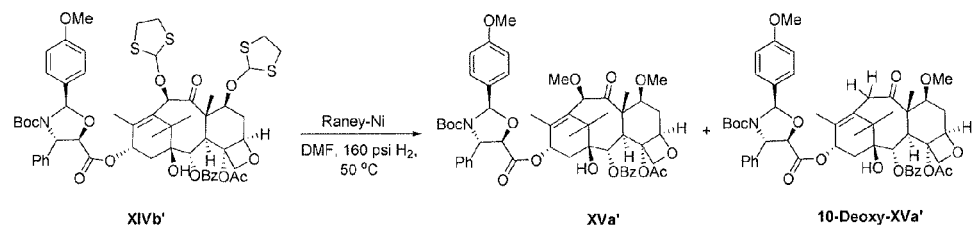
FIG. 25 shows the synthetic scheme for the preparation of XVa' from XIVb'.

XVa' was prepared according to FIG. 25. XIVb' (5 g, 4.4 mmol) in DMF (75 mL) was hydrogenolysed in the presence of a suspension of Raney Nickel (approximately 100 g) at 50° C. for 15 h under an atmosphere of hydrogen gas at 160 psi. After the reaction was complete as determined by HPLC analysis. HPLC analysis of the product mixture showed 61 area % XVa' and 17 area % 10-Deoxy-XVa'. The product mixture was filtered through a pad of diatomaceous earth and washed with EtOAc (250 mL). HPLC assay indicated a 47% yield of XVa' was obtained. The organic layer was evaporated under vacuum to provide an oil that was purified by column chromatography eluting with EtOAc/n-heptane (1:1.5) to furnish XVa' (1.7 g, 40%) as a white solid. 10-Deoxy-XVa' (520 mg, 13%) was also isolated in a separate fraction as a white solid.

Preparation of XVa' from XIVc'

Figure 26:
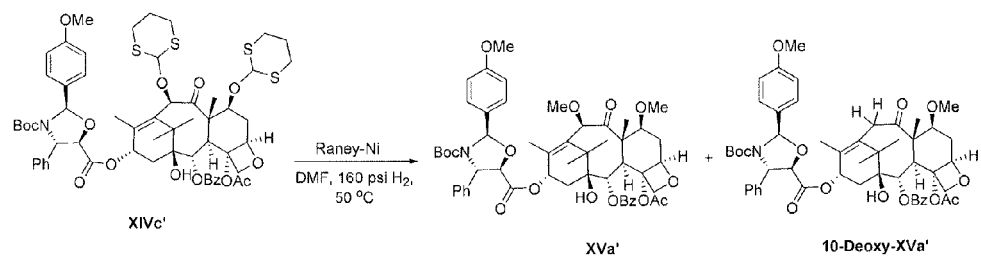
FIG. 26 shows the synthetic scheme for the preparation of XVa' from XIVc'.

XVa' was prepared according to FIG. 26. XIVc' (50 mg, 0.05 mmol) in DMF (1 mL) was hydrogenolysed in the presence of a suspension of Raney Nickel (approximately 1.2 g) at 50° C. for 23.5 h under an atmosphere of hydrogen gas at 160 psi. After the reaction was complete as determined by TLC analysis, the product mixture was filtered through a pad of diatomaceous earth and washed with EtOAc (2.5 mL). HPLC assay indicated a 19% yield of XVa' had been achieved. HPLC analysis of the product mixture showed 28 area % XVa' and 23 area % 10-Deoxy-XVa'.

Preparation of XVa' from XIVa

Figure 27:
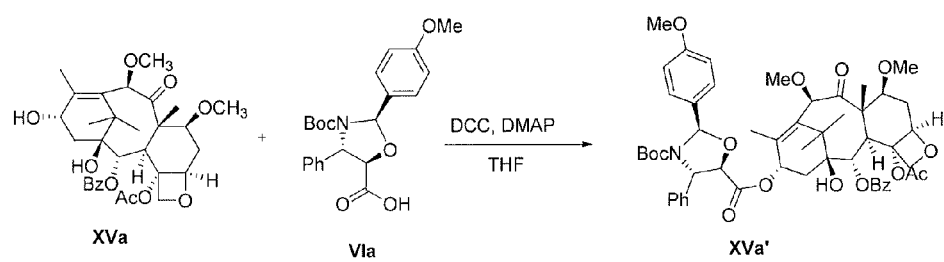
FIG. 27 shows the synthetic scheme for the preparation of XVa' from XVa.

XVa' was prepared according to FIG. 27. To a THF (2 mL) solution of XVa (200 mg, 0.35 mmol), DMAP (9 mg, 0.67 mmol) and VIa (280 mg, 0.70 mmol) was added dicyclohexylcarbodiimide (181 mg, 0.88 mmol). The solution was stirred for 2 hours at room temperature. 1 M HCl (1 mL) was added and the product mixture was filtered and extracted with EtOAc (5 mL). The extract was washed with NaHCO$_3$ (1 mL) and then water (1 mL) and the organic layer was evaporated under vacuum to provide an oil that was purified by column chromatography eluting with EtOAc/n-heptane (1.5:1) to furnish XVa' (303 mg, 91%) as a white solid.

Example 3

Preparation of Cabazitaxel from XVa'

Figure 28:
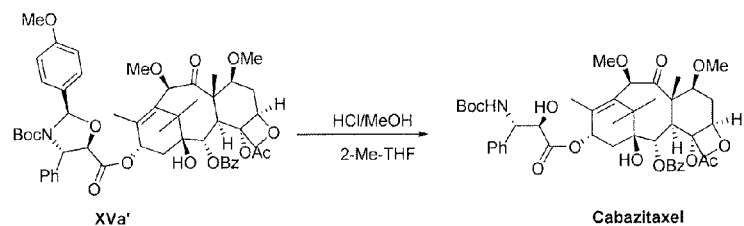
FIG. 28 shows the synthesis of cabazitaxel.

Cabazitaxel was prepared according to FIG. 28. A mixture of XVa' (6.8 g, 7.13 mmol) in 2-methyltetrahydrofuran (105 mL), 12 M HCl (10 mL) and MeOH (34 mL) was stirred at room temperature until the reaction was complete (about 0.5 hour), as determined by HPLC analysis. The pH of the aqueous phase was adjusted to about 7 by addition of 1M NaOH. The layers were separated and the organic phase was concentrated until about 3 volumes remained. The aqueous phase extracted with EtOAc (200 mL) and the extract was combined with the prior mentioned concentrate and was evaporated under vacuum to provide an oil that was purified by column chromatography with EtOAc/n-heptane (1:1.5) providing cabazitaxel (4.8 g, 81%) as a white solid. $R_f$=0.4 (TLC, eluent: EtOAc/n-heptane (2/1, v/v)); m.p. 163-165° C.; IR (KBr) 3539, 3375, 2974, 2930, 2825, 1719 cm$^{-1}$; $[\alpha]_{21}^D$=−36 (c=0.5; methanol); $^1$H NMR (400 MHz, CDCl$_3$) δ 8.04 (dd, J=8, 1.2 Hz, 2H), 7.63-7.59 (m, 1H), 7.51-7.47 (m, 2H), 7.40-7.39 (m, 4H), 7.34-7.28 (m, 1H), 6.24-6.20 (m, 1H), 5.63 (d, J=7.2 Hz, 1H), 5.51 (m, 1H), 5.29-5.26 (m, 1H), 4.98 (d, J=8.4 Hz, 1H), 4.81 (s, 1H), 4.63 (m, 1H), 4.29 (d, J=8.4 Hz, 1H), 4.19 (d, J=8.4 Hz, 1H), 3.88-3.84 (m, 1H), 3.82 (d, J=6.8 Hz, 1H), 3.58 (m, 1H), 3.46 (s, 3H), 3.31 (s, 3H), 2.72-2.68 (m, 1H), 2.37 (s, 3H), 2.30-2.27 (m, 2H), 1.89 (s, 3H), 1.89-1.76 (m, 2H), 1.72 (s, 3H), 1.37 (s, 9H), 1.22 (s, 3H), 1.21 (s, 3H); $^{13}$C NMR (100 MHz, CDCl$_3$) δ 205.0, 127.7, 170.4, 166.9, 155.3, 138.7, 138.4, 135.6, 133.6, 130.1, 129.2, 128.8, 128.6, 126.8, 884.1, 82.6, 81.7, 80.7, 80.2, 78.7, 76.5, 74.6, 73.7, 72.5, 57.3, 57.0, 56.9, 47.7, 43.3, 35.3, 32.1, 32.1, 28.2, 26.8, 22.7, 20.7, 14.6, 10.3

Example 4

Preparation of XVa Using a 7-O-1,3-benzodithiolan-2-yl Derivative of 10-DAB

Preparation of 7-O-triethylsilyl-10-DAB (XVIIa)

Figure 29:
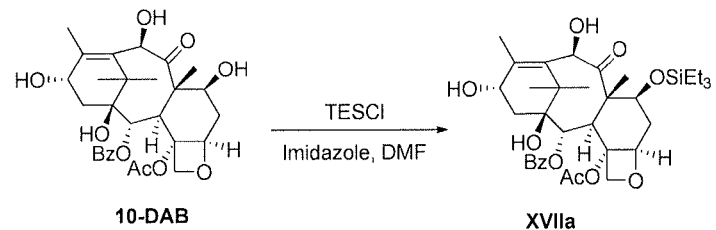
FIG. 29 shows the synthesis of XVIIa.

XVIIa was prepared according to FIG. 29. To a chilled (−10 to −15° C.) mixture of 10-DAB (8.0 g, 14.7 mmol) and imidazole (3.1 g, 45.6 mmol) in DMF (55 mL) was slowly added triethylsilyl chloride (3.7 g, 25.0 mmol). After string at −10 to −15° C. until the reaction was complete, the product mixture was slowly added into a mixture of water (224 mL) and toluene (41 mL) and was stirred for at least 20 minutes. n-Heptane (80 mL) was added to the slurry and the mixture is stirred for at least 20 minutes. The product was filtered and the wet cake was dissolved in EtOAc (320 mL). The solution was washed with saturated NaCl solution (32 mL), the EtOAc layer was separated and concentrated under reduced pressure until most of the EtOAc was removed. n-Heptane (80 mL) was added and the mixture was concentrated under reduced pressure until the majority of the EtOAc and n-heptane mixture was removed. n-Heptane (80 mL) was added, stirred and XVIIa was isolated by filtration and dried under vacuum at 45 to 65° C. to provide XVIIa (about 9.2 g, 95% yield). $^1$H NMR (400 MHz, CDCl$_3$) δ 8.13 (d, J=8.0 Hz, 2H), 7.61 (m, 1H), 7.48 (m, 2H), 5.62 (d, J=7.2 Hz, 1H), 5.19 (s, 1H), 4.97 (dd, J=13.2, 1.6 Hz, 1H), 4.88 (m, 1H), 4.43 (dd, J=10.8, 6.8 Hz, 1H), 4.32 (dd, J=86, 8.8 Hz, 2H), 4.32 (m, 1H), 3.97 (d, J=7.2 Hz, 1H), 2.53-2.45 (m, 1H), 2.30 (s, 3H), 2.29-2.27 (m, 2H), 2.13 (s, 3H), 195-1.88 (m, 1H), 1.76 (s, 3H), 1.60 (m, 1H), 1.1 (m, 6H), 0.98-0.93 (m, 9H), 0.63-0.55 (m, 6H).

Preparation of 10-O-methyl-7-O-triethylsilyl-10-DAB (XVIIIa)

Figure 30:
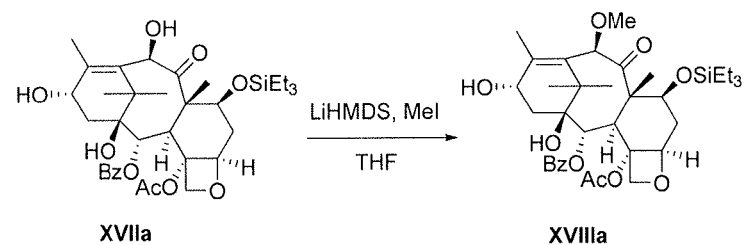
FIG. 30 shows the synthesis of XVIIIa.

XVIIIa was prepared according to FIG. 30. To a solution of XVIIa (21.6 g, 32.9 mmol) in THF (173 mL) was added 1.06 M LiHMDS in THF (46.0 mL, 52.6 mmol) at −40° C. After stirring for 10 min at −40° C., methyl iodide (12.3 mL, 263.2 mmol) was added dropwise. The mixture was warmed to 0° C. over a 30-60 minutes period and was then slowly allowed to warm to room temperature and stirred overnight. Saturated aqueous NH$_4$Cl solution was added and the mixture was extracted with THF. The organic layer was concentrated to 3 volumes and THF (60 mL) and n-heptane (300 mL) were added. The precipitated solid was filtered and dried under vacuum at 55° C. to provide XVIIIa (about 18.1 g, 82% yield). $^1$H NMR (400 MHz, CDCl$_3$) δ 8.13 (d, J=8.0, 2H), 7.62 (t, J=7.2, 1H), 7.49 (t, J=7.6 Hz, 2H), 5.62 (d, J=6.8 Hz, 1H), 4.98-4.97 (m, 1H), 4.96 (s, 1H), 4.97-4.93 (m, 1H), 4.45 (m, 1H), 4.24 (dd, J=60, 8.4 Hz, 2H), 3.90 (d, J=7.2 Hz, 1H), 3.43 (s, 3H), 2.52-2.47 (m, 1H), 2.31 (s, 3H), 2.31-2.28 (m, 1H), 2.13 (s, 3H), 2.16-2.13 (m, 1H), 1.94-1.89 (m, 1H), 1.70 (s, 3H), 1.19 (s, 3H), 1.09 (s, 3H), 0.90 (m, 6H), 0.88 (m, 6H), 0.63-0.55 (m, 5H).

Preparation of 10-O-methyl-10-DAB (XIXa)

Figure 31:
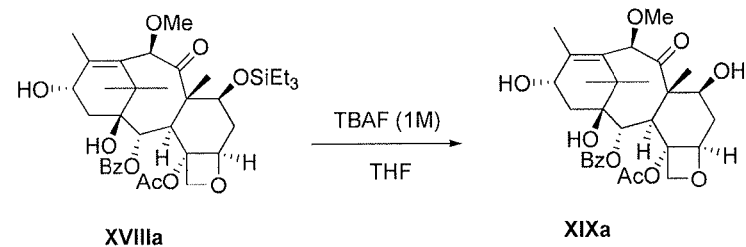
FIG. 31 shows the synthesis of XIXa.

XIXa was prepared according to FIG. 31. A solution of XVIIIa (40.3 g, 59.4 mmol) and 1 M TBAF in THF (118 mL, 118.8 mmol) in THF (200 mL) was stirred at 23° C. for 1.5 hours. Water (400 mL) was added and the mixture was completely concentrated to provide a solid which was isolated by filtration and was then washed with methyl tert-butyl ether (MTBE). The solid was dissolved in THF (120 mL) and was precipitated by the addition of water (120 mL). The solid was isolated by filtration and dried under vacuum at 55° C. to provide XIXa (about 27.8 g, 83% yield). $^1$H NMR (400 MHz, DMSO) δ 8.02 (dd, J=8.4, 6.8 Hz, 2H), 7.68-7.64 (m, 1H), 7.57 (t, J=7.6 Hz, 2H), 5.39 (d, J=6.8 Hz, 1H), 5.28 (m, 1H), 5.01 (m, 1H), 4.92 (d, J=8.0 Hz, 1H) 4.89 (s, 1H), 4.68-4.64 (m, 1H), 4.15-4.11 (m, 1H), 4.02 (s, 2H), 3.75 (d, J=6.8 Hz, 1H), 3.31 (s, 3H), 2.52-2.50 (m, 2H), 2.23-2.22 (m, 1H), 2.19-2.16 (m, 4H), 2.19 (s, 3H), 1.65-1.63 (m, 1H), 1.48 (s, 3H), 0.95-0.92 (m, 6H).

Preparation of 10-O-methyl-7-O-1,3-benzodithiolan-2-yl-10-DAB (XVIa)

Figure 32:
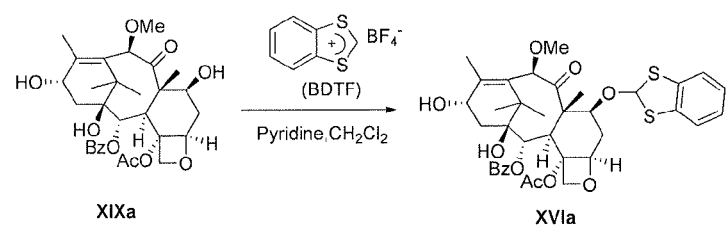
FIG. 32 shows the synthesis of XVIa.

XVIa was prepared according to FIG. 32. To a suspension of XIXa (69 mg, 0.12 mmol) in anhydrous DCM (1.5 mL) was added 1,3-benzodithiolium tetrafluoroborate (84 mg, 0.36 mmol) and anhydrous pyridine (58 μL, 0.72 mmol). The resulting mixture was stirred at ambient temperature for 22 hours. A further portion of 1,3-benzodithiolium tetrafluoroborate (84 mg, 0.36 mmol) and anhydrous pyridine (58 μL, 0.72 mmol) was added to the mixture. After the reaction was complete, the product mixture was diluted with DCM (10 mL) and triethylamine (250 μL, 1.8 mmol) and was stirred for an additional 15 min. The reaction mixture was washed with 1 M HCl (10 mL) and then washed with water (10 mL), dried over MgSO$_4$, filtered and concentrated under reduced pressure. The residue was chromatographed on a column of silica gel eluting with n-heptane/EtOAc (1:1) to provide XVIa (40 mg, 47%).

Preparation of 7,10-di-O-methyl-10-DAB (XVa) from XVIa

Figure 33:
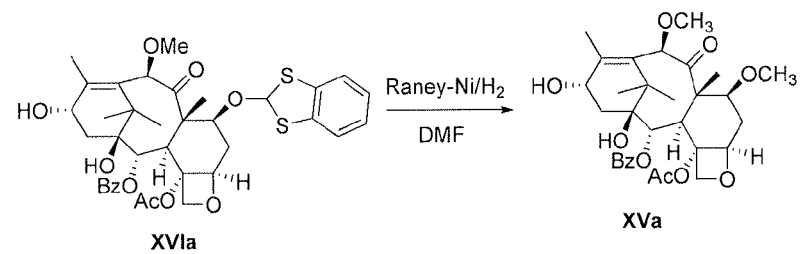
FIG. 33 shows the synthesis of XVa from XVIa.

XVa was prepared according to FIG. 33. A solution of XVIa (22 mg, 0.03 mmol) in DMF (1 mL) was hydrogenolysed in the presence of a suspension of Raney Nickel (approximately 700 mg) at ambient temperature for 15 hours under an atmosphere of hydrogen gas (3.4 atm pressure). The mixture was filtered through a pad of diatomaceous earth and washed with EtOAc 30 mL) and the filtrate was evaporated under vacuum to provide a solid. The solid was triturated with EtOAc 10 mL) and filtered to provide XVa.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing a compound of formula (I)

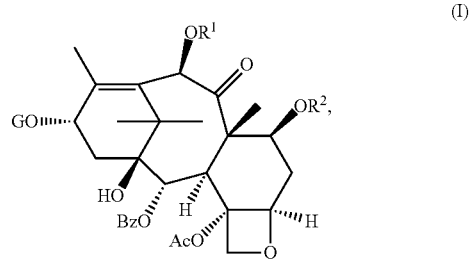

said process comprising:
a) contacting 10-deacetylbaccatin III of formula (II)

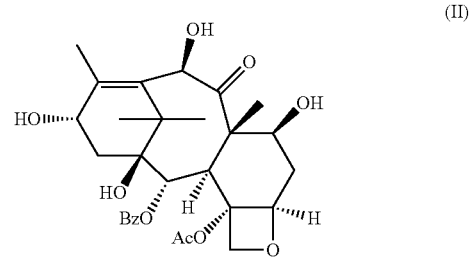

with a 1,3-dithiolane derivative or a 1,3-dithiane derivative, to obtain a compound of formula (V)

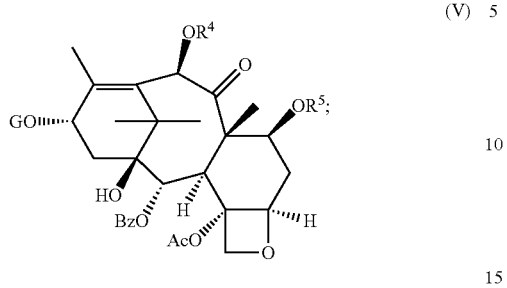
(V)

and b) converting said compound of formula (V) to a compound of formula (I); wherein
each of $R^1$ and $R^2$ is independently branched or unbranched $C_1$-$C_6$ alkyl;
each of $R^4$ and $R^5$, which may be identical or different, is 1,3-dithian-2-yl, 1,3-dithiolan-2-yl, 1,3-dithiolan-4-en-2-yl, or 1,3-benzodithiolan-2-yl; and
G is H.

2. A process according to claim 1, wherein step a) is conducted in the presence of a weak base selected from the group consisting of pyridine; a tertiary amine; 1,8-diazabicyclo [5.4.0] undec-7-ene; 1,5-diazabicyclo [4.3.0] non-5-ene ; a saturated heterocyclic base; a pyridine derivative; or an aromatic heterocyclic base.

3. A process according to claim 1, wherein the converting to the compound of formula (I) comprises hydrodesulfurization with a hydrodesulfurization agent, wherein the hydrodesulfurization agent is selected from the group consisting of Raney Nickel, [NiCl$_2$]6H$_2$O in the presence of NaBH$_4$, and a transition metal.

4. A process for preparing a compound of formula (I)

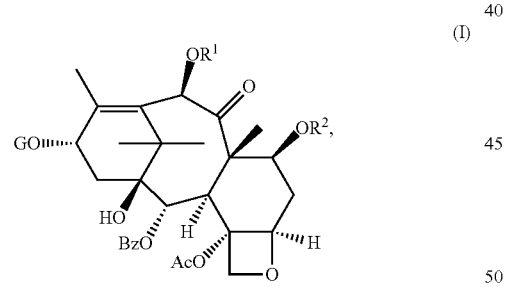
(I)

said process comprising:
a) contacting 10-deacetylbaccatin III of formula (II)

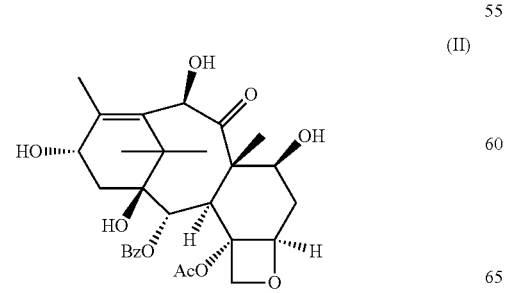
(II)

with a compound of (R″)$_3$SiY (IVX) to obtain a compound of formula (VIII)

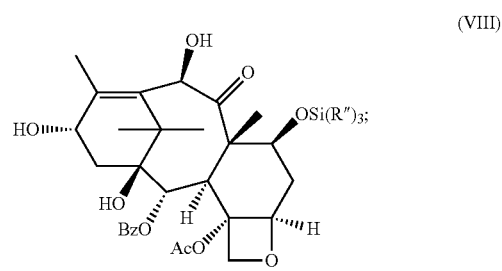
(VIII)

b) contacting the compound of formula (VIII) with an alkyl halide, a dialkyl sulfate, a trialkyl oxonium salt or an alkyl sulfonate in the presence of a strong base to obtain a compound of formula (IX)

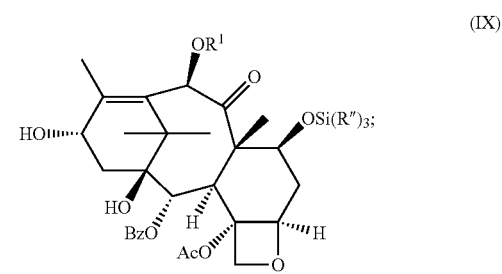
(IX)

c) contacting the compound of foimula (IX) with a desilylation agent to obtain a compound of formula (X)

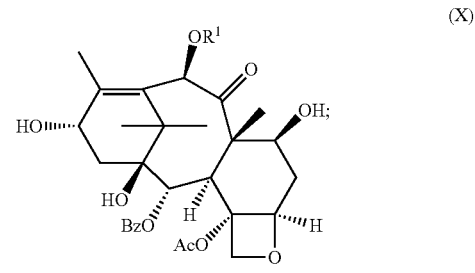
(X)

d) contacting the compound of formula (X) with a dithiane derivative or a dithiolane derivative to obtain a compound of formula (VII)

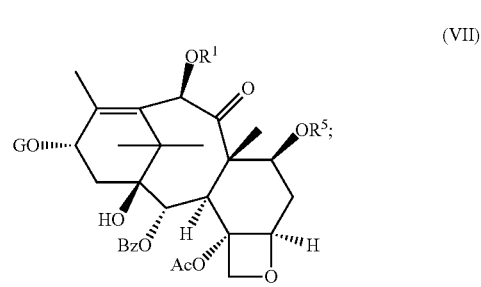
(VII)

and
e) converting the compound of formula (VII) to the compound of formula (I); wherein
each of $R^1$ and $R^2$ is independently branched or unbranched $C_1$-$C_6$ alkyl;
$R^5$ is 1,3-dithian-2-yl, 1,3-dithiolan-2-yl, 1,3-dithiolan-4-en-2-yl, or 1,3-benzodithiolan-2-yl;
R" is independently branched or unbranched $C_1$-$C_6$, or $C_6$-$C_{10}$ aryl;
G is H; and
Y is a halide.

5. A process according to claim 4, wherein the strong base is selected from the group consisting of an alkali metal hydride, an alkali metal alkoxide, silver oxide, a mixture of an alkali metal amide and an alkali metal tert-butoxide, and a mixture of an alkyllithium and an alkali metal tert-butoxide.

6. A process according to claim 4, wherein the step a) is carried out at not more than 0° C.

7. A process according to claim 4, wherein the converting to the compound of formula (I) comprises hydrodesulfurization with a hydrodesulfurization agent, wherein the hydrodesulfurization agent is selected from the group consisting of Raney Nickel, [NiCl$_2$]6H$_2$O in the presence of NaBH$_4$, and a transition metal.

8. A process according to claim 1, wherein the compound of formula (I) is further converted into cabazitaxel, with the proviso that each of $R^1$ and $R^2$ is a methyl group.

9. A process for preparing a compound of formula (XIII)

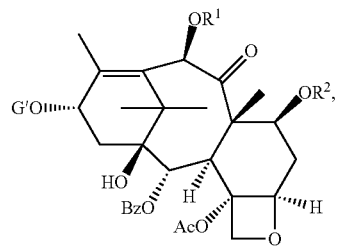

wherein G' is a side chain of formula (IV')

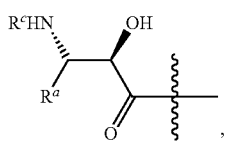

said process comprising converting a compound of formula (VA)

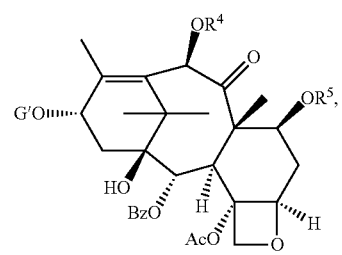

wherein G' is a side chain of formula (IV)

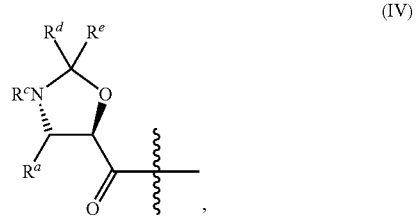

to the compound of formula (XIII); wherein
each of $R^1$ and $R^2$ is independently branched or unbranched $C_1$-$C_6$ alkyl;
each of $R^4$ and $R^5$ is independently 1,3-dithian-2-yl, 1,3-dithiolan-2-yl, 1,3-dithiolan-4-en-2-yl, or 1,3-benzodithiol-2-yl;
$R^a$ is branched or unbranched $C_1$-$C_8$ alkyl; branched or unbranched $C_2$-$C_8$ alkenyl; branched or unbranched $C_2$-$C_8$ alkynyl; or phenyl or naphthyl optionally substituted with one or more substituents selected from the group consisting of halo, alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonyl, carbamoyl, alkylcarbamoyl, dialkylcarbamoyl, cyano, nitro and trifluoromethyl;
$R^c$ is benzoyl optionally substituted with one or more substituents independently selected from the group consisting of halo, $C_1$-$C_4$ alkyl, $C_1$-$C_4$ alkoxy, and trifluoromethyl; thenoyl; furoyl; or
$R^c$ is $R^3$—O—CO— wherein
$R^3$ is $C_1$-$C_8$ alkyl, $C_2$-$C_8$ alkenyl, $C_3$-$C_8$ alkynyl, $C_3$-$C_6$ cycloalkyl, or $C_4$-$C_6$ cycloalkenyl; each of which is optionally substituted with one or more substituents selected from the group consisting of cyano; carboxyl; $C_1$-$C_4$ alkoxycarbonyl; and phenyl optionally with one or more of halo, $C_1$-$C_4$ alkyl, and $C_1$-$C_4$ alkoxy; or
$R^3$ is phenyl or naphthyl, each of which is optionally substituted with one or more substituents selected from halo and $C_1$-$C_4$ alkyl; or
$R^3$ is 5-membered heteroaryl; and
$R^d$ and $R^e$ are independently selected from hydrogen, alkyl, aryl, halo, alkoxy, arylalkyl, haloalkyl and haloaryl; or taken together $R^d$ and $R^e$ form a 4- to 7-membered ring.

10. A process according to claim 9, wherein the converting to the compound of formula (XIII) comprises hydrodesulfurization and deprotection of the side chain protecting group in one reaction step or in separate reactions steps.

11. A process according to claim 9, wherein the compound of formula (VA) is prepared by contacting a compound of formula (III)

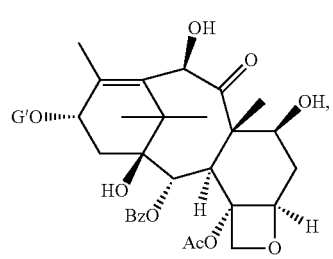

wherein G' is a side chain of formula (IV)

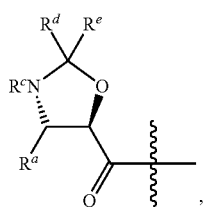

with a 1,3-dithiolane derivative or a 1,3-dithiane derivative, to obtain the compound of formula (VA).

12. A process according to claim 9, wherein the compound of formula (VA) is prepared by esterifying a compound of formula (V)

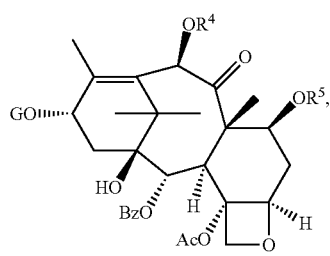

wherein G is H, with a compound of formula (VI)

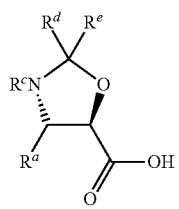

to obtain the compound of formula (VA); wherein each of $R^4$ and $R^5$ is independently 1,3-dithian-2-yl, 1,3-dithiolan-2-yl, 1,3-dithiolan-4-en-2-yl or 1,3-benzodithio1-2-yl.

13. A process according to claim 1, wherein the contacting step with a 1,3-dithiolane derivative or a 1,3-dithiane derivative is conducted in a solvent selected from the group consisting of dichloromethane, chloroform, 1,2-dichloroethane, tetrahydrofuran, 2-methyltetrahydrofuran, acetonitrile, acetone, pyridine, and mixtures thereof.

14. A process according to claim 13, wherein the solvent is dichloromethane.

15. A process according to claim 1, wherein contacting compounds of formula II or III with a 1,3-dithiolane derivative or a 1,3-dithiane derivative is conducted at a temperature of from about 10° C. to 35° C.

16. A process according to claim 10, wherein the hydrodesulfurization is conducted in the presence of a reducing agent or in the presence of a hydrogen source.

17. A process according to claim 10, wherein the hydrodesulfurization is conducted in a range of solvents including ethanol (EtOH), n-butanol (n-BuOH), ethylene glycol, ethyl acetate (EtOAc), tetrahydrofuran (THF), 1,4-dioxane, acetonitrile (MeCN), dimethylformamide (DMF), N-methyl-2-pyrrolidone (NMP), 1,3-dimethyl-3,4,5,6-tetrahydro-2(1H)-pyrimidinone (DMPU), or mixtures thereof.

18. A process according to claim 17, wherein the solvent is dimethylformamide (DMF).

19. A process according to claim 10, wherein the hydrodesulfurization comprises contacting the compound of formula (VA) with Raney Nickel in the presence of a hydrogen source.

20. A process according to claim 10, wherein the hydrodesulfurization is conducted under a pressurized atmosphere of hydrogen gas at from about 20 psi to about 200 psi.

21. A process according to claim 10, wherein the hydrodesulfurization is conducted at a temperature of from about 20° C. to about 70° C.

22. A process for preparing a compound of formula (XIII)

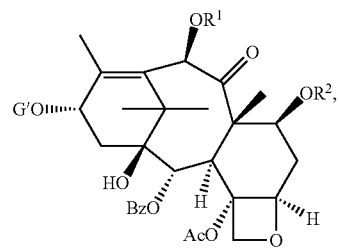

wherein G' is a side chain of formula (IV')

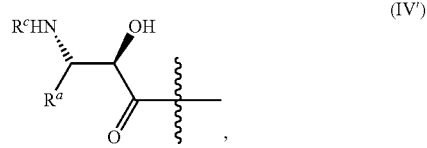

said process comprising:
a) esterifying a compound of formula (IX)

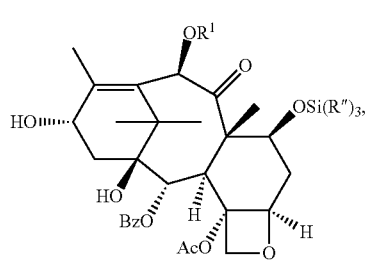

with a compound of formula (VI)

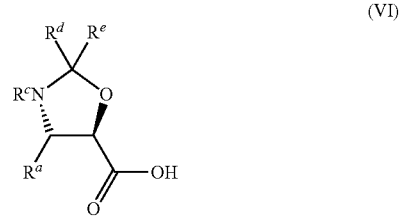

to obtain a compound of formula (IXA)

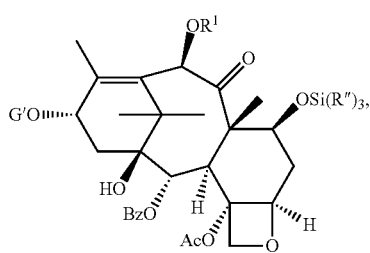

wherein G is a side chain of formula (IV)

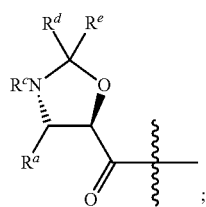

b) converting the compound of formula (IXA) to a compound of formula (XA)

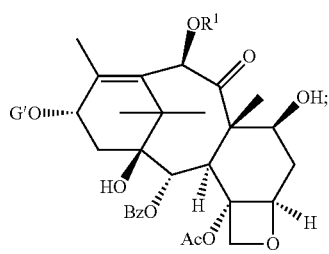

c) converting the compound of formula (XA) by treatment with a 1,3-dithiolane derivative or a 1,3-dithiane derivative, to a compound of (XIIA)

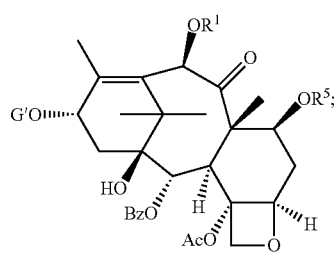

and
d) converting the compound of formula (XIIA) to the compound of formula (XIII); wherein
each of $R^1$ and $R^2$ is independently $C_1$-$C_6$ alkyl;
$R^5$ is 1,3-dithian-2-yl, 1,3-dithiolan-2-yl, 1,3-dithiolan-4-en-2-yl, or 1,3-benzodithiol-2-yl;
each R" is independently branched or unbranched $C_1$-$C_6$ alkyl or $C_6$-$C_{10}$ aryl;
$R^a$ is branched or unbranched $C_1$-$C_8$ alkyl; branched or unbranched $C_2$-$C_8$ alkenyl; branched or unbranched $C_2$-$C_8$ alkynyl; or phenyl or naphthyl optionally substituted with one or more substituents selected from the group consisting of halo, alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonyl, carbamoyl, alkylcarbarnoyl, dialkylcarbamoyl, cyano, nitro and trifluoromethyl;
$R^c$ is benzoyl optionally substituted with one or more substituents independently selected from the group consisting of halo, $C_1$-$C_4$ alkyl, $C_1$-$C_4$ alkoxy, and trifluoromethyl; thenoyl; furoyl; or
$R^c$ is $R^3$—O—CO— wherein
$R^3$ is $C_1$-$C_8$ alkyl, $C_2$-$C_8$ alkenyl, $C_3$-$C_8$ alkynyl, $C_3$-$C_6$ cycloalkyl, or $C_4$-$C_6$ cycloalkenyl; each of which is optionally substituted with one or more substituents selected from the group consisting of cyano; carboxyl; $C_1$-$C_4$ alkoxycarbonyl; and phenyl optionally with one or more of halo, $C_1$-$C_4$ alkyl, and $C_1$-$C_4$ alkoxy; or
$R^3$ is phenyl or naphthyl, each of which is optionally substituted with one or more substituents selected from halo and $C_1$-$C_4$ alkyl; or
$R^3$ is 5-membered heteroaryl; and
$R^d$ and $R^e$ are independently selected from hydrogen, alkyl, aryl, halo, alkoxy, arylalkyl, haloalkyl and haloaryl; or taken together $R^d$ and $R^e$ foini a 4- to 7-membered ring.

23. A process according to claim 22, wherein the step d) comprises hydrodesulfurization and deprotection of the side chain protecting group in one reaction step or in separate reactions steps.

24. A process according to claim 1, wherein each of $R^1$ and $R^2$, which may be identical or different, is an unbranched or a branched $C_1$-$C_3$ alkyl chain.

25. A process according to claim 1, wherein each of $R^1$ and $R^2$ is a methyl group.

26. A process according to claim 22, wherein $R^a$ is Ph, $R^c$ is tert-butyloxycarbonyl (BOC), $R^d$ is H and $R^e$ is 4-methoxyphenyl.

27. A process according to claim 1, wherein the 1,3-dithiolane derivative or 1,3-dithiane derivative is selected from the group consisting of a 1,3-dithian-2-ylium salt; a 1,3-dithiolan-2-ylium salt; a 1,3-dithiolium salt; a 1,3-benzodithiolium salt; a 1,3-dithiane derivative that possesses a leaving group, X, at the C2 position; or a 1,3-dithiolane derivative that possesses a leaving group, X, at the C2 position.

* * * * *